(12) United States Patent
Taka et al.

(10) Patent No.: US 9,005,770 B2
(45) Date of Patent: Apr. 14, 2015

(54) COMPOUND, ELECTROLUMINESCENT ELEMENT CONTAINING THE SAME, ILLUMINATING DEVICE AND DISPLAY DEVICE

(75) Inventors: Hideo Taka, Tokyo (JP); Hiroshi Kita, Tokyo (JP); Tatsuo Tanaka, Kanagawa (JP)

(73) Assignee: Konica Minolta Holdings, Inc., Tokyo (JP)

( * ) Notice: Subject to any disclaimer, the term of this patent is extended or adjusted under 35 U.S.C. 154(b) by 1267 days.

(21) Appl. No.: 12/297,594

(22) PCT Filed: Apr. 17, 2007

(86) PCT No.: PCT/JP2007/058324
§ 371 (c)(1),
(2), (4) Date: Oct. 17, 2008

(87) PCT Pub. No.: WO2007/123111
PCT Pub. Date: Nov. 1, 2007

(65) Prior Publication Data
US 2009/0102370 A1  Apr. 23, 2009

(30) Foreign Application Priority Data
Apr. 20, 2006   (JP) .................................. 2006-116468

(51) Int. Cl.
| H01L 51/54 | (2006.01) |
| C09K 11/06 | (2006.01) |
| C07D 233/58 | (2006.01) |
| C07D 233/64 | (2006.01) |
| C07D 239/20 | (2006.01) |
| C07F 15/00 | (2006.01) |
| H05B 33/14 | (2006.01) |
| H01L 51/50 | (2006.01) |
| H01L 51/00 | (2006.01) |

(52) U.S. Cl.
CPC ........... *C07D 233/58* (2013.01); *H01L 51/5016* (2013.01); *C07D 233/64* (2013.01); *C07D 239/20* (2013.01); *C07F 15/0033* (2013.01); *C07F 15/006* (2013.01); *C07F 15/0073* (2013.01); *C07F 15/0086* (2013.01); *C09K 11/06* (2013.01); *C09K 2211/1029* (2013.01); *C09K 2211/1033* (2013.01); *C09K 2211/1037* (2013.01); *C09K 2211/1044* (2013.01); *C09K 2211/1048* (2013.01); *C09K 2211/1051* (2013.01); *C09K 2211/1059* (2013.01); *C09K 2211/1062* (2013.01); *C09K 2211/1066* (2013.01); *C09K 2211/1074* (2013.01); *C09K 2211/1088* (2013.01); *C09K 2211/1092* (2013.01); *C09K 2211/185* (2013.01); *H01L 51/0037* (2013.01); *H01L 51/0081* (2013.01); *H01L 51/0085* (2013.01); *H01L 51/0087* (2013.01); *H01L 51/5012* (2013.01); *H01L 2251/308* (2013.01); *H05B 33/14* (2013.01)

(58) Field of Classification Search
None
See application file for complete search history.

(56) References Cited

U.S. PATENT DOCUMENTS

| 7,902,374 B2 * | 3/2011 | Lin et al. .................... 548/103 |
| 2003/0068536 A1 * | 4/2003 | Tsuboyama et al. ......... 428/704 |
| 2004/0253478 A1 * | 12/2004 | Thompson et al. ........... 428/690 |
| 2006/0251923 A1 * | 11/2006 | Lin et al. .................... 428/690 |

FOREIGN PATENT DOCUMENTS

| JP | 2003342235 | | 12/2003 |
| JP | 2005-68110 A | * | 3/2005 |
| JP | 2005053912 | | 3/2005 |
| WO | 02066552 | | 8/2002 |
| WO | 2004085450 | | 10/2004 |
| WO | WO 2004/101707 A1 | * | 11/2004 |
| WO | 2007069542 | | 6/2007 |

OTHER PUBLICATIONS

Machine translation of JP 2005-068110 (Mar. 2005).*

* cited by examiner

*Primary Examiner* — Marie R. Yamnitzky
(74) *Attorney, Agent, or Firm* — Lucas & Mercanti, LLP

(57) ABSTRACT

Provided are a novel compound, an organic EL element which contains such novel compound and has a high external extraction quantum efficiency and a long service life, an illuminating apparatus and a display apparatus.

10 Claims, 2 Drawing Sheets

LIGHT

LIGHT

US 9,005,770 B2

COMPOUND, ELECTROLUMINESCENT ELEMENT CONTAINING THE SAME, ILLUMINATING DEVICE AND DISPLAY DEVICE

This is a U.S. National Phase Application under 35 U.S.C. 371 of International Application PCT/JP2007/058324 filed on Apr. 17, 2007, which claims the priority of Japanese Application No. 2006-116468, filed Apr. 20, 2006, the entire content of both Applications are hereby incorporated by reference.

TECHNICAL FIELD

The present invention relates to a compound, an electroluminescent element containing it, an illuminating device and a display device.

TECHNICAL BACKGROUND

Electroluminescent displays are known as light emitting type electronic display device (ELD). An inorganic electroluminescent element (inorganic EL element) and an organic electroluminescent element (organic EL element) are cited as the constituting element of the ELD. The inorganic EL element has been used as a planar light source though high alternative voltage is required for driving such the light emitting device. The organic EL element is an element having a light emission layer placed between a cathode and an anode, in which electrons and positive holes are injected into the light emission layer and excitons are generated by recombination of them, and fluorescence or phosphorescence light is emitted on the occasion of quenching of the excitons. Such the device is noted because which can emit light by application of a voltage of several to several tens volts, and has wide viewing angle and high visibility since it is a self light emission type, and is completely solid state thin device suitable for space saving and portable appliance.

However, in an organic electroluminescence in view of the future practical application, desired has been development of an organic EL element which efficiently emits at a high luminance with a low electric consumption.

In Japanese Patent No. 3093796, a slight amount of a fluorescent substance has been doped in a stilbene derivative, distyrylarylene derivative or a tristyrylarylene derivative, to achieve improved emission luminance and a prolonged lifetime of an element. Further, there are known such as an element having an organic emission layer comprising a 8-hydroxyquinoline aluminum complex as a host compound which is doped with a slight amount of a fluorescent substance (for example, JP-A 63-264692 (hereinafter, JP-A refers to Japanese Patent Publication Open to Public Inspection No.)) and an element having an organic emission layer comprising a 8-hydroxyquinoline aluminum complex as a host compound which is doped with quinacridone type dye (for example, JP-A 3-255190).

In the case of utilizing emission from an excited singlet as described above, since a generation ratio of a singlet exciton to a triplet exciton is 1:3, that is, a generation probability of an emitting exciton species is 25% and a light taking out efficiency is approximately 20%, the limit of a quantum efficiency (next) of taking out is said to be 5%.

However, since an organic EL element which utilizes phosphorescence from an excited triplet has been reported from Princeton University (M. A. Baldo et al., Nature vol. 395, pp. 151-154 (1998)), researches on materials exhibiting phosphorescence at room temperature have come to be active.

For example, it is also disclosed in A. Baldo et al., Nature, vol. 403, No. 17, pp. 750-753 (2000), and U.S. Pat. No. 6,097,147.

Since the upper limit of internal quantum efficiency becomes 100% by utilization of an excited triplet, which is principally 4 times of the case of an excited singlet, it may be possible to achieve almost the same ability as a cooled cathode ray tube to attract attention also for an illumination application.

For example, in such as S. Lamansky et al., J. Am. Chem. Soc., vol. 123, p. 4304 (2001), many compounds mainly belonging to heavy metal complexes such as iridium complexes have been synthesized and studied.

Further, in aforesaid, A. Baldo et al., Nature, vol. 403, No. 17, pp. 750-753 (2000), utilization of tris(2-phenylpyridine) iridium as a dopant has been studied.

In addition to these, M. E. Tompson et al., at The 10th International Workshops on Inorganic and Organic Electroluminescence (EL'00, Hamamatsu), have studied to utilize $L_2Ir$ (acac) such as $(ppy)_2Ir(acac)$ as a dopant, Moon-Jae Youn. Og., Tetsuo Tsutsui et al., also at The 10th International Workshops on Inorganic and Organic Electroluminescence (EL'00, Hamamatsu), have studied utilization of such as tris (2-(p-tolyl)pyridine)iridium $(Ir(ptpy)_3)$ and tris(benzo[h] quinoline)iridium $(Ir(bzq)_3)$ (these metal complexes are generally referred to as orthometalated iridium complexes.).

Further, in also the aforesaid, S. Lamansky eat al., J. Am. Chem. Soc., vol. 123, p. 4304 (2001), studies have been carried out to prepare an element utilizing various types of iridium complexes.

Further, to obtain high emission efficiency, Ikai et al., at The 10th International Workshops on Inorganic and Organic Electroluminescence (EL'00, Hamamatsu) utilized a hole transporting compound as a host of a phosphorescent compound. Further, M. E. Tompson et al. utilized various types of electron transporting materials as a host of a phosphorescent compound doped with a new iridium complex.

An orthometalated complex provided with platinum instead of iridium as a center metal is also attracting attention. With respect to these types of complexes, many examples having a characteristic ligand are known by JP A 2002-332291, JP A 2002-332292, JP A 2002-338588, JP A 2002-226495, JP A 2002-234894, and Inorganic Chemistry, Vol. 41, No. 12, 3055-3066 (2002).

In any case, emission luminance and emission efficiency are significantly improved compared to conventional elements because the emitting light arises from phosphorescence, however, there has been a problem of a poor emission lifetime of the element compared to conventional elements. It is hard to achieve an emission of a short wavelength and an improvement of an emission lifetime of the element for a phosphorescent emission material provided with a high efficiency. At present state, it cannot be achieved a level of a practical use.

With respect to shortening of emission wavelength, heretofore, there have been known introduction of an electron attracting group such as a fluorine atom, a trifluoromethyl group, or a cyano group as a substituent group into phenylpyridine, and introduction of a ligand of such as picolinic acid or of a pyrazabole type by WO 02/15645, JP A 2003-123982, JP A 2002-11797B, JP A 2003-146996, WO 04/016711, Inorganic Chemistry, Vol. 41, No. 12, 3055-3066 (2002), Applied Physics Letters Vol. 79, 2082 (2001), Applied Physics Letters Vol. 83, 3818 (2003), and New Journal of Chemistry, vol. 26, 1171, (2002). However, when an emission wavelength is shortened to achieve blue color by utilizing these substitution effects, a high efficiency may be achieved while emission lifetime will be greatly deteriorated, which requires further improvement to overcome the trade-off relationship.

Light emitting material having high phosphorescence efficiency is difficult to make the emission light wavelength shorter and improve emission lifetime, and therefore, it does not display performance sufficient for practical use.

A metal complex having phenyl pyrazole as a ligand, for example, patent documents 1 and 2. While the substitution manner of phenyl pyrazole with phenyl group is improved in emission lifetime, it is not sufficient and there is a room to improve emission efficiency.

On the other hand, the vapor deposition process which is usually applied in the production of the organic EL device using a low molecular weight compound causes problems of production equipment and energy efficiency when the organic EL element having enlarged area is manufactured, and it is thought that a printing method including a ink-jet printing method and a screen printing method or a coating method such as a spin coating method and a cast coating method are desirable. Though an organic metal complex having dendrimer portion (see, Patent Document 3), and an organic metal complex fixed in polymer chain (see, Patent Document 4) are known as a phosphorescence material suitable for printing method or coating method, they are insufficient and improvement is desired in view of emission efficiency or life time.

Patent Document 1: WO 04/085450
Patent Document 2: JP A 2005-053912
Patent Document 3: WO 02/066552
Patent Document 4: JP A 2003-342235

DISCLOSURE OF THE INVENTION

Problems to be Solved

In view of the foregoing, the present invention was achieved. An object of the present invention is to provide a novel compound, an organic EL element which incorporates aforesaid novel compound, and exhibits a high external extraction quantum yield, and a long lifetime, an illuminating device, and a display device.

The above object of the present invention was achieved via the following embodiments.

1. A compound characterized by having the partial structure represented by following Formula (1).

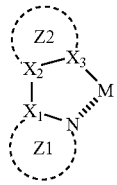

Formula (1)

Wherein $X_1$, $X_2$, and $X_3$ each represents a carbon atom or a nitrogen atom; Z1 represents a group of atoms which are necessary to form a 5-membered aromatic heterocyclic ring; Z2 represents a group of atoms which are necessary to form a cyclopentadiene ring or an aromatic hydrocarbon ring, or a group of atoms which is necessary to from a 5- to 6-membered aromatic heterocyclic ring; and M represents Ir or Pt. Aforesaid Z1 or Z2 has at least one solubility controlling group or film formation controlling group, and the aforesaid solubility controlling group or film formation controlling group represents an aromatic hydrocarbon ring having a substituent, an aromatic heterocyclyl group having a substituent, or an alkyl group having at least 6 carbon atoms.

2. A compound characterized by having the partial structure represented by following Formula (2):

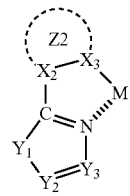

Formula (2)

wherein $X_2$ and $X_3$ each represents a carbon atom or a nitrogen atom; $Y_1$ represents $-N(R_1)-$, $-O-$, or $-S-$; $Y_2$ and $Y_3$ each represents a carbon atom or a nitrogen atom; Z2 represents a group of atoms which are necessary to form a 6-membered aromatic hydrocarbon ring, or a group of atoms which are necessary to form a 5- to 6-membered aromatic heterocyclic ring; and M represents Ir or Pt, while aforesaid $R_1$ represents a hydrogen atom, an alkyl group, an alkenyl group, an alkynyl group, a cycloalkyl group, an aromatic hydrocarbon ring, an aromatic heterocyclyl group, or a heterocyclyl group. The aforesaid partial structure has at least one of the solubility controlling group and the film formation controlling group, and the aforesaid solubility controlling group or film formation controlling group represents an aromatic hydrocarbon group having a substituent, an aromatic heterocyclyl group having a substituent, or an alkyl group having at least 6 carbon atoms.

3. A compound characterized by having the partial structure represented by Formula (3):

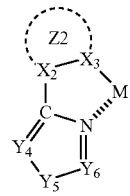

Formula (3)

wherein $X_2$ and $X_3$ each represents a carbon atom or a nitrogen atom; $Y_5$ represents $-N(R_1)-$, $-O-$, or $-S-$; $Y_4$ and $Y_6$ each represents a carbon atom or a nitrogen atom; Z2 represents a group of atoms which are necessary to form a 6-membered aromatic hydrocarbon ring, or a group of atoms which are necessary to form a 5- to 6-membered aromatic heterocyclic ring; and M represents Ir or Pt; while aforesaid $R_1$ represents a hydrogen atom, an alkyl group, an alkenyl group, an alkynyl group, a cycloalkyl group, an aromatic hydrocarbon group, an aromatic heterocyclyl group, or a heterocyclyl group. The aforesaid partial structure has at least one of the solubility controlling group and the film formation controlling group, while the aforesaid solubility controlling group or the film formation controlling group represents an aromatic hydrocarbon group having a substituent, an aromatic heterocyclyl group having a substituent, or an alkyl group having at least 6 carbon atoms.

4. A compound characterized by having the partial structure represented by following Formula (4):

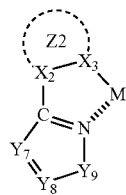

Formula (4)

wherein $X_2$ and $X_3$ each represents a carbon atom or a nitrogen atom; $Y_9$ represents —N($R_1$)—, —O—, or —S—; $Y_7$ and $Y_8$ each represents a carbon atom or a nitrogen atom; Z2 represents a group of atoms which are necessary to form a 6-membered aromatic hydrocarbon ring, or a group of atoms which are necessary to form a 5- to 6-membered aromatic heterocyclic ring; and M represents Ir or Pt; while aforesaid $R_1$ represents a hydrogen atom, an alkyl group, an alkenyl group, an alkynyl group, a cycloalkyl group, an aromatic hydrocarbon group, an aromatic heterocyclyl group, or a heterocyclyl group. The aforesaid partial structure has at least one of the solubility controlling group and the film formation controlling group, while the aforesaid solubility controlling group or film formation controlling group represents an aromatic hydrocarbon group having a substituent, an aromatic heterocyclyl group having a substituent, or an alkyl group having at least 6 carbon atoms.

5. A compound characterized by having the partial structure represented by following Formula (5):

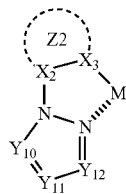

Formula (5)

wherein $X_2$ and $X_3$ each represents a carbon atom or a nitrogen atom; $Y_{10}$, $Y_{11}$, and $Y_{12}$ each represents a carbon atom or a nitrogen atom; Z2 represents a group of atoms which are necessary to form a 6-membered aromatic hydrocarbon ring, or a group of atoms which are necessary to form a 5- to 6-membered aromatic heterocyclic ring; and M represents Ir or Pt. The aforesaid partial structure has at least one of the solubility controlling group and the film formation controlling group, while the aforesaid solubility controlling group or film formation controlling group represents an aromatic hydrocarbon group having a substituent, an aromatic heterocyclyl group having a substituent, or an alkyl group having at least 6 carbon atoms.

6. The compound, described in any one of 1.-5. above, wherein aforesaid Z2 is a phenyl group.

7. A compound characterized by having a partial structure of any one of following Formulas (6)-(8).

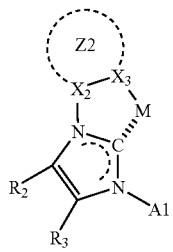

Formula (6)

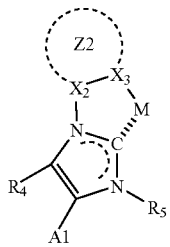

Formula (7)

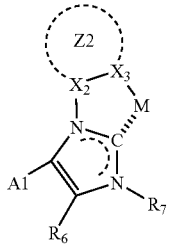

Formula (8)

wherein $X_2$ and $X_3$ each represents a carbon atom or a nitrogen atom; $R_2$, $R_3$, $R_4$, $R_5$, $R_6$, and $R_7$ each represents a hydrogen atom, or a substituent; Z2 represents a group of atoms which are necessary to form a 6-membered aromatic hydrocarbon ring, or a group of atoms which are necessary to form a 5- to 6-membered aromatic heterocyclic ring; and M represents Ir or Pt. A1 represents an aromatic hydrocarbon group which incorporates a solubility controlling group or a film formation controlling group, the aforesaid solubility controlling group or film formation controlling group represents an aromatic hydrocarbon group having a substituent, an aromatic heterocyclyl group having a substituent, or an alkyl group having at least 6 carbon atoms.

8. The compound, described in any one of 1.-7. above, wherein the aforesaid solubility controlling group or film formation controlling group is an aromatic hydrocarbon ring group having a substituent or an aromatic heterocyclyl group having a substituent.

9. The compound, described in any of 1.-8. above, which contains at least two of the aforesaid solubility controlling group or film formation controlling.

10. The compound, described in any of 1.-9. above, wherein the formula weight of the aforesaid solubility controlling group or film formation controlling group is at least 115.

11. In an organic electroluminescent element which comprises a support substrate having thereon at least an anode and a cathode, and at least one organic layer including a light emitting layer between the anode and the cathode, an organic electroluminescent element wherein at least one of the organic layers contains a compound described in any one of Formulas (1)-(8).

12. In an organic electroluminescent element which incorporates a support substrate having thereon organic layers which incorporate at least an anode and a cathode and incorporate at least one light emitting layer between the aforesaid anode and the aforesaid cathode, an organic electroluminescent element wherein at least one of the aforesaid light emitting layers incorporates the compound described in any one of aforesaid Formulas (1)-(8).

13. The organic electroluminescent element, described in 11. or 12. above, wherein the aforesaid light emitting layer is subjected to film formation via a coating method.

14. An illuminating device characterized by having the organic electroluminescent element, described in any one of 11.-13. above.

15. A display device characterized by having the organic electroluminescent element, described in any one of 11.-13. above.

Advantage of the Invention

According to the present invention, it was possible to provide a novel compound, an organic EL element which incorporates the aforesaid novel compound, and exhibits a high external extraction quantum yield, and a long lifetime, an illuminating device, and a display device.

OPTIMAL EMBODIMENT OF THE INVENTION

Figure 1:
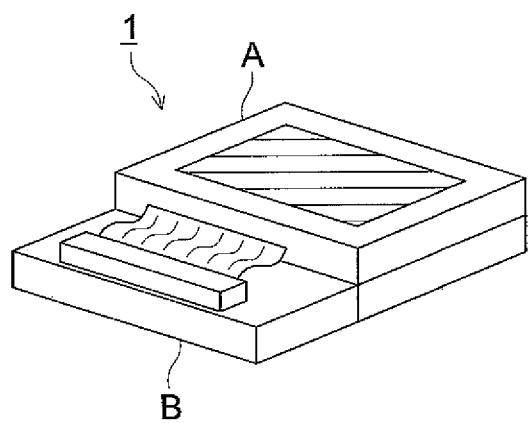
FIG. 1 is a schematic view showing one example of a display device composed of organic EL elements.

In the compounds of the present invention, by realizing the constitution described in any one of items 1-11 above, success was achieved to prepare the compounds (also referred to as metal complexes) which are effective to form organic electroluminescent elements. By employing the aforesaid compounds, it was possible to prepare organic electroluminescent elements (organic EL elements), which exhibited a high external extraction quantum yield, and a long element lifetime (enhanced durability). Further, success was also achieved to prepare display devices and illuminating devices, both of which were fitted with the aforesaid organic EL elements.

Each of the constituting elements according to the present invention will now be sequentially detailed.

<<Compounds Incorporating Partial Structure Represented by Formula (1)>>

Description will be made with regard to compounds incorporating the partial structure represented by Formula (1) of the present invention.

In Formula (1), listed as the 5-membered aromatic heterocyclic ring represented by Z1 are an oxazole ring, an oxadiazole ring, an oxatriazole ring, an isoxazole ring, a tetrazole ring, a thiazole ring, a thiatriazole ring, an isothiazole ring, a thiophene ring, a furan ring, a pyrrole ring, an imidazole ring, a pyrazole ring, and a triazole ring.

In Formula (1), listed as the 6-membered aromatic hydrocarbon ring represented by Z2 is a benzene ring.

In Formula (1), listed as the 5- to G-membered aromatic heterocyclic king represented by Z2 are an oxazole ring, an oxadiazole ring, an oxatriazole ring, an isoxazole ring, a tetrazole ring, a thiadiazole ring, a thiatriazole ring, an isothiazole ring, a thiophene ring, a furan ring, a pyrrole ring, an imidazole ring, a pyrazole ring, a triazole ring, a pyridine ring, a pyridazine ring, a pyrimidine ring, a pyrazine ring, a diazine ring, and a triazine ring.

In Formula (1), the benzene ring is most preferably employed.

<<Solubility Controlling Groups or Film Formation Controlling Groups>>

Solubility controlling groups or film formation controlling groups according to the present invention will now be described.

In the partial structure represented by Formula (1), aforesaid Z7 or Z2 has at least one of the solubility controlling groups or film formation controlling groups.

As used herein, "solubility controlling groups or film formation controlling groups" according to the present invention include: an aromatic hydrocarbon ring group, having a substituent (also called an aromatic carbon ring group or an aryl group such as a phenyl group, a p-chlorophenyl group, a mesityl group, a tolyl group, a xylyl group, a naphthyl group, an anthryl group, an azulenyl group, an acenaphthenyl group, a fluorenyl group, a phenanthryl group, an indenyl group, a pyrenyl group, a biphenylyl group, or a metaterphenylyl group); an aromatic heterocyclyl group having a substituent (such as a furyl group, a thienyl group, a pyridyl group, a pyridazinyl group, a pyrimidinyl group, a pyrazinyl group, a triazinyl group, an imidazolyl group, a pyrazolyl group, a thiazolyl group, a quinazolinyl group, a carbazolyl group, a carbolinyl group, a diazacarbazolyl group (referring to the group in which any one of carbon atoms constituting the carboline ring of the aforesaid carbolinyl group is replaced with a nitrogen atom), or a phthalazinyl group), and an alkyl group having at least 6 carbon atoms (which may have a straight or branched chain and of the alkyl groups described below as an substituent, those having at least 6 carbon atoms may be employed). Of these, preferably listed are the phenyl group, the biphenyl group, and a metaterphenylyl group, each of which has a substituent.

Further, as the above substituent, preferred are an alkyl group (for example, a methyl group, an ethyl group, a propyl group, an isopropyl group, a tert-butyl group, a pentyl group, a xylyl group, an octyl group, a dodecyl group, a tridecyl group, a tetradecyl group, and a pentadecyl group); an alkoxy group (for example, a methoxy group, an ethoxy group, a propyloxy group, an isopropyloxy group, a tert-butyloxy group, a pentyloxy group, a hexyloxy group, an octyloxy group, and a dodecyloxy group), and more preferred are a branched alkyl group (for example, an isopropyl group, a tert-butyl group), or a branched alkoxy group (for example, an isopropyloxy group and a tert-butyloxy group).

(Effects Realized by Having Solubility Controlling Group or Film Formation Controlling Agent)

In the compounds having the partial structure represented by Formula (1), via introduction of at least one of the above "solubility controlling agents or film formation controlling agents", planar and stereoscopic spread of molecules results, whereby film production is enhanced, while concentration quenching is retarded, whereby effects are realized to enable host-free.

Incidentally, effects, which are realized via introduction of the solubility controlling agent or the film formation controlling agents according to the present invention, may be the same as those realized by each of the compounds represented by following Formulas (2)-(8).

<<Compounds Incorporating Partial Structure Represented by Formula (2)>>

Compounds incorporating the partial structure represented by Formula (2) of the present invention will now be described.

In —N($R_1$)— of Formula (2), examples of the alkyl group represented by $R_1$ include a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group.

In —N($R_1$)— of Formula (2), examples of the alkenyl group represented by $R_1$ include a vinyl group, an allyl group, a 1-propenyl group, a 2-butenyl group, a 1,3-butadienyl group, a 2-pentenyl group, and an isopropenyl group.

In —N($R_1$)— of Formula (2), examples of the alkynyl group represented by $R_1$ include an ethynyl group and a propargyl group.

In —N($R_1$)— of Formula (2), examples of the cycloalkyl group represented by $R_1$ include a cyclopentyl group and a cyclohexyl group.

In —N($R_1$)— of Formula (2), examples of the aromatic hydrocarbon group (also referred to as the aryl group or the aromatic hydrocarbon ring group) represented by $R_1$ include a phenyl group, a p-chlorophenyl group, a mesityl group, a tolyl group, a xylyl group, a naphthyl group, an anthryl group, an azulenyl group, an acenaphthenyl group, a fluolenyl group, a phenanthryl group, an indenyl group, a pyrenyl group, a biphenyl group, and a metaterphenylyl group.

In —N($R_1$)— of Formula (2), examples of the aromatic heterocyclyl group represented by $R_1$ include a furyl group, a thienyl group, a pyridyl group, a pyridazinyl group, a pyrazinyl group. a triazinyl group, an imidazolyl group, a pyrazolyl group, a thiazolyl group, a quinazolinyl group, a carbazolyl group, a carbolinyl group, a diazacarbazolyl group (which represents one in which any one of carbon atoms which constitute the carboline ring of the above carbolinyl group), and a phthalazinyl group.

In —N($R_1$)— of Formula (2), examples of the heterocyclyl group represented by $R_1$ include a pyrrolidyl group, an imidazolidyl group, a morpholyl group, and an oxazolidyl group.

In —N($R_1$)— of Formula (2), the 6-membered aromatic hydrocarbon rings and 5- to 6-membered aromatic heterocyclic rings represented by Z2 are the same as defined for corresponding 6-membered aromatic hydrocarbon rings and 5- to 6-membered aromatic heterocycles represented by Z2 in Formula (1).

Further, the partial structure represented by Formula (2) incorporates at least one of the solubility controlling groups or the film formation controlling groups. These are the same as defined for the corresponding solubility controlling agents or film formation controlling agents described in Formula (1).

<<Compounds Incorporating Partial Structure Represented by Formula (3)>>

Compounds incorporating the partial structure represented by Formula (3) of the present invention will now be described.

In —N($R_1$)— of Formula (3), each of the alkyl group, the alkenyl group, the alkynyl group, the cycloalkyl group, the aromatic hydrocarbon group, the aromatic heterocyclyl group or the heterocyclyl group represented by $R_1$ is the same as defined for the group represented by $R_1$ in above Formula (2).

In Formula (3), each of the 6-membered aromatic hydrocarbon rings and the 5- to 6-membered aromatic heterocyclic rings represented by Z2 the same as defined for the 6-membered aromatic hydrocarbon ring and the 5- to 6-membered aromatic heterocyclic ring represented by Z2 in Formula (1).

Further, the partial structure represented by Formula (3) incorporates at least one of the solubility controlling group or the film formation controlling group, each of which is the same as defined for the solubility controlling agent or the film formation controlling agent described in Formula (1).

<<Compounds Incorporating Partial Structure Represented by Formula (4)>>

Compounds incorporating the partial structure represented by Formula (4) will now be described.

In —N($R_1$)— of Formula (4), the alkyl group, the alkenyl group, the alkynyl group, the cycloalkyl group, the aromatic hydrocarbon group, the aromatic heterocyclyl group, or the heterocyclyl group, represented by $R_1$, is the same as defined for the group represented by $R_1$ in above Formula (2).

In Formula (4), each of the 6-membered aromatic hydrocarbon rings, and the 5- to 6-membered aromatic heterocyclic rings, represented by Z2 is the same as defined for the 6-membered aromatic hydrocarbon ring and the 5- to 6-membered aromatic heterocyclic ring represented by Z2 in Formula (1).

Further, the partial structure represented by Formula (4) incorporates at least one of the solubility controlling group or the film formation controlling group, each of which is the same as defined for the solubility controlling agent or the film formation controlling agent described in Formula (1).

<<Compounds Incorporating Partial Structure Represented by Formula (5)>>

Compounds incorporating the partial structure represented by Formula (4) will now be described.

In Formula (5), each of the 6-membered aromatic hydrocarbon rings, and the 5 to 6-membered aromatic heterocyclic rings, represented by Z2, is the same as defined for the 6-membered aromatic hydrocarbon ring and the 5- to 6-membered aromatic heterocyclic ring represented by Z2 in Formula (1).

Further, the partial structure represented by Formula (5) incorporates at least one of the solubility controlling group or the film formation controlling group, each of which is the same as defined for the solubility controlling agent or the film formation controlling agent described in Formula (1).

<<Compounds Incorporating Partial Structure Represented by Formulas (6), (7), or (8)>>

Compounds incorporating the partial structure, represented by Formulas (6) (7), and (8), will now be described.

In Formulas (6), (7), and (8), the substituents represented by each of $R_2$, $R_3$, $R_4$, $R_5$, $R_6$, and $R_7$ include an alkyl group (for example, a methyl group, an ethyl group, a propyl group, an isopropyl group, a tert-butyl group, a pentyl group, a hexyl group, an octyl group, a dodecyl group, a tridecyl group, a tetradecyl group, or a pentadecyl group); a cycloalkyl group (for example, a cyclopentyl group or a cyclohexyl group); an alkenyl group (for example, a vinyl group, an allyl group, a 1-propenyl group, a 2-butenyl group, a 1,3-butadienyl group, a 2-pentenyl group, or an isopropenyl group); an alkynyl group (for example, an ethynyl group or a propargyl group); an aromatic hydrocarbon group (also referred to as an aromatic carbon ring group or an aryl group, for example, a phenyl group, a p-chlorophenyl group, a mesityl group, a tolyl group, a xylyl group, a naphthyl group, an anthryl group, an azulenyl group, an acenaphthenyl group, a fluorenyl group, a phenanthryl group, an indenyl group, a pyrenyl group, and a biphenylyl group); an aromatic heterocyclyl group (for example, a furyl group, a thienyl group, a pyridyl group, a pyridazinyl group, a pyrimidinyl group, a pyrazinyl group, a triazinyl group, an imidazolyl group, a pyrazolyl group, a thiazolyl group, a quinazolinyl group, a carbazolyl group, a carbolinyl group, and a diazacarbazolyl group (referring to the group in which any one of carbon atoms constituting the carboline ring of the aforesaid carbolinyl group is replaced with a nitrogen atom), and a phthalazinyl group); a heterocyclyl group (for example, a pyrrolidyl group, an imidazolyl group, a morpholyl group, and an oxazolidyl group) an alkoxy group (for example, a methoxy group, an ethoxy group, a propyloxy group, a pentyloxy group, a hexyloxy group, an octyloxy group, and a dodecyloxy group); a cycloalkoxy group (for example, a cyclopentyloxy group and a cyclohexyloxy group); an aryloxy group (for example, a phenoxy group and a naphthyloxy group); an alkylthio group (for example, a methylthio group, an ethylthio group, a propylthio group, a pentylthio group, a hexylthio group, an octylthio group, and a dodecylthio group); a cycloalkylthio group (for example, a cyclopentylthio group and a cyclohexylthio group); an arylthio group (for example, a phenylthio group and a naphthylthio group); an alkoxycarbonyl group (for example, a methyloxycarbonyl group, an ethyloxycarbonyl group, a butyloxycarbonyl group, an octyloxycarbonyl group, and a dodecyloxycarbonyl group); an aryloxycarbonyl group (for example, a phenyloxycarbonyl group, a naphthyloxycarbonyl group); a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, and a 2-pyridylaminosulfonyl group); an acyl group (for example, an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, and a pyridylcarbonyl group); an acyloxy group (for example, an acetyloxy group, an ethylcarbonyloxy group, a butylcarbonyloxy group, an octylcarbonyloxy group, a dodecylcarbonyloxy group, and a phenylcarbonyloxy group); an amido group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octyldarbonylamino group, a dodecylcarbonylamino group, a phenylcarbonylamino group, and a naphthylcarbonylamino group); a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group, and a 2-pyridylaminocarbonyl group); a ureido group (for example, a methylureido group, an ethylureido group, a pentylureido group, a cyclohexylureido group, an octylureido group, a dodecylureido group, a phenylureido group, a naphthylureido group, and a 2-pyridylaminoureido group); a sulfinyl group (for example, a methylsulfinyl group, an ethylsulfinyl group, a butylsulfinyl group, a cyclohexylsulfinyl group, a 2-ethylhexylsulfinyl group, a dodecylsulfinyl group, a phenylsulfinyl group, a naphthylsulfinyl group, and a 2-pyridylsulfinyl group); an alkylsulfonyl group (for example, a methylsulfonyl group, an ethylsulfonyl group, a butylsulfonyl group, a cyclohexylsulfonyl group, a 2-ethylhexylsulfonyl group, and a dodecylsulfonyl group); an arylsulfonyl or heteroarylsulfonyl group (for example, a phenylsulfonyl group, a naphthylsulfonyl group, and a 2-pyridylsulfonyl group); an amino group (for example, an amino group, an ethylamino group, a dimethylamino group, a butylamino group, a cyclopentylamino group, a 2-ethylhexylamino group, a dodecylamino group, an anilino group, a naphthylamino group, and a 2-pyridylamino group); a halogen atom (for example, a fluorine atom, a chlorine atom, and a bromine atom); a fluorinated hydrocarbon group (for example, a fluoromethyl group, a trifluoromethyl group, a pentafluoroethyl group, and a pentafluorophenyl group); a cyano group, a nitro group, a hydroxyl group, a mercapto group; a silyl group (for example, a trimethylsilyl group, a triisopropylsilyl group, a triphenylsilyl group, and a phenyldiethylsilyl group); and a phosphono group.

These substituents may be further substituted with the aforesaid substituents. Further, a plurality of these substituents may be combined with each other to form a ring.

In Formulas (6), (7), and (8), each of the 6-membered aromatic hydrocarbon rings and 5- to 6-membered aromatic heterocyclic rings represented by Z2 is the same as defined for each of the 6-membered aromatic hydrocarbon ring and 5- to 6-membered aromatic heterocyclic ring, represented by Z2 in Formula (1).

In Formulas (6), (7), and (8), each of the solubility controlling groups or film formation controlling groups, represented by A1, is the same as defined for the solubility controlling group or the film formation controlling group described in Formula (1).

Listed below are Specific Examples BD-1-BD-545 of compounds incorporating the partial structure represented by any one of Formulas (1)-(8) of the present invention, however the present invention is not limited thereto.

Structural parts which constitute BD-1-BD-545 are listed below.

| Complex | Center Metal | Ligand 1 | Number | Ligand 2 | Number |
|---|---|---|---|---|---|
| BD-1 | Ir | L-1 | 3 | — | — |
| BD-2 | Ir | L-1 | 2 | L-231 | 1 |
| BD-3 | Ir | L-2 | 3 | — | — |
| BD-4 | Ir | L-2 | 2 | L-231 | 1 |
| BD-5 | Ir | L-2 | 2 | L-233 | 1 |
| BD-6 | Ir | L-3 | 3 | — | — |
| BD-7 | Ir | L-3 | 2 | L-231 | 1 |
| BD-8 | Ir | L-4 | 3 | — | — |
| BD-9 | Ir | L-4 | 2 | L-231 | 1 |
| BD-10 | Ir | L-5 | 3 | — | — |
| BD-11 | Ir | L-5 | 2 | L-231 | 1 |
| BD-12 | Ir | L-6 | 3 | — | — |
| BD-13 | Ir | L-6 | 2 | L-231 | 1 |
| BD-14 | Ir | L-7 | 3 | — | — |
| BD-15 | Ir | L-7 | 2 | L-231 | 1 |
| BD-16 | Ir | L-8 | 3 | — | — |
| BD-17 | Ir | L-8 | 2 | L-231 | 1 |
| BD-18 | Ir | L-9 | 3 | — | — |
| BD-19 | Ir | L-9 | 2 | L-231 | 1 |
| BD-20 | Ir | L-10 | 3 | — | — |
| BD-21 | Ir | L-10 | 2 | L-231 | 1 |
| BD-22 | Ir | L-11 | 3 | — | — |
| BD-23 | Ir | L-11 | 2 | L-231 | 1 |
| BD-24 | Ir | L-12 | 3 | — | — |
| BD-25 | Ir | L-12 | 2 | L-231 | 1 |
| BD-26 | Ir | L-13 | 3 | — | — |
| BD-27 | Ir | L-13 | 2 | L-231 | 1 |
| BD-28 | Ir | L-14 | 3 | — | — |
| BD-29 | Ir | L-14 | 2 | L-231 | 1 |
| BD-30 | Ir | L-15 | 3 | — | — |
| BD-31 | Ir | L-15 | 2 | L-231 | 1 |
| BD-32 | Ir | L-16 | 3 | — | — |
| BD-33 | Ir | L-16 | 2 | L-231 | 1 |
| BD-34 | Ir | L-17 | 3 | — | — |
| BD-35 | Ir | L-17 | 2 | L-231 | 1 |
| BD-36 | Ir | L-18 | 3 | — | — |
| BD-37 | Ir | L-18 | 2 | L-231 | 1 |
| BD-38 | Ir | L-19 | 3 | — | — |
| BD-39 | Ir | L-19 | 2 | L-231 | 1 |
| BD-40 | Ir | L-20 | 3 | — | — |
| BD-41 | Ir | L-20 | 2 | L-231 | 1 |
| BD-42 | Ir | L-21 | 3 | — | — |
| BD-43 | Ir | L-21 | 2 | L-231 | 1 |
| BD-44 | Ir | L-22 | 3 | — | — |
| BD-45 | Ir | L-22 | 2 | L-231 | 1 |

-continued

| Complex | Center Metal | Ligand 1 | Number | Ligand 2 | Number |
|---|---|---|---|---|---|
| BD-46 | Ir | L-23 | 3 | — | — |
| BD-47 | Ir | L-23 | 2 | L-231 | 1 |
| BD-48 | Ir | L-24 | 3 | — | — |
| BD-49 | Ir | L-24 | 2 | L-231 | 1 |
| BD-50 | Ir | L-25 | 3 | — | — |
| BD-51 | Ir | L-25 | 2 | L-231 | 1 |
| BD-52 | Ir | L-26 | 3 | — | — |
| BD-53 | Ir | L-26 | 2 | L-231 | 1 |
| BD-54 | Ir | L-27 | 3 | — | — |
| BD-55 | Ir | L-27 | 2 | L-231 | 1 |
| BD-56 | Ir | L-28 | 3 | — | — |
| BD-57 | Ir | L-28 | 2 | L-231 | 1 |
| BD-58 | Ir | L-29 | 3 | — | — |
| BD-59 | Ir | L-29 | 2 | L-231 | 1 |
| BD-60 | Ir | L-30 | 3 | — | — |
| BD-61 | Ir | L-30 | 2 | L-231 | 1 |
| BD-62 | Ir | L-31 | 3 | — | — |
| BD-63 | Ir | L-31 | 2 | L-231 | 1 |
| BD-64 | Ir | L-32 | 3 | — | — |
| BD-65 | Ir | L-32 | 2 | L-231 | 1 |
| BD-66 | Ir | L-33 | 3 | — | — |
| BD-67 | Ir | L-33 | 2 | L-231 | 1 |
| BD-68 | Ir | L-34 | 3 | — | — |
| BD-69 | Ir | L-34 | 2 | L-231 | 1 |
| BD-70 | Ir | L-35 | 3 | — | — |
| BD-71 | Ir | L-35 | 2 | L-231 | 1 |
| BD-72 | Ir | L-36 | 3 | — | — |
| BD-73 | Ir | L-36 | 2 | L-231 | 1 |
| BD-74 | Ir | L-37 | 3 | — | — |
| BD-75 | Ir | L-37 | 2 | L-231 | 1 |
| BD-76 | Ir | L-38 | 3 | — | — |
| BD-77 | Ir | L-38 | 2 | L-231 | 1 |
| BD-78 | Ir | L-39 | 3 | — | — |
| BD-79 | Ir | L-39 | 2 | L-231 | 1 |
| BD-80 | Ir | L-40 | 3 | — | — |
| BD-81 | Ir | L-40 | 2 | L-231 | 1 |
| BD-82 | Ir | L-41 | 3 | — | — |
| BD-83 | Ir | L-41 | 2 | L-231 | 1 |
| BD-84 | Ir | L-42 | 3 | — | — |
| BD-85 | Ir | L-42 | 2 | L-231 | 1 |
| BD-86 | Ir | L-43 | 3 | — | — |
| BD-87 | Ir | L-43 | 2 | L-231 | 1 |
| BD-88 | Ir | L-44 | 3 | — | — |
| BD-89 | Ir | L-44 | 2 | L-231 | 1 |
| BD-90 | Ir | L-45 | 3 | — | — |
| BD-91 | Ir | L-45 | 2 | L-231 | 1 |
| BD-92 | Ir | L-46 | 3 | — | — |
| BD-93 | Ir | L-46 | 2 | L-231 | 1 |
| BD-94 | Ir | L-47 | 3 | — | — |
| BD-95 | Ir | L-47 | 2 | L-231 | 1 |
| BD-96 | Ir | L-48 | 3 | — | — |
| BD-97 | Ir | L-48 | 2 | L-231 | 1 |
| BD-98 | Ir | L-48 | 2 | L-232 | 1 |
| BD-99 | Ir | L-48 | 2 | L-233 | 1 |
| BD-100 | Ir | L-48 | 2 | L-234 | 1 |
| BD-101 | Ir | L-48 | 1 | L-234 | 2 |
| BD-102 | Ir | L-49 | 3 | — | — |
| BD-103 | Ir | L-49 | 2 | L-231 | 1 |
| BD-104 | Ir | L-50 | 3 | — | — |
| BD-105 | Ir | L-50 | 2 | L-231 | 1 |
| BD-106 | Ir | L-51 | 3 | — | — |
| BD-107 | Ir | L-51 | 2 | L-231 | 1 |
| BD-108 | Ir | L-52 | 3 | — | — |
| BD-109 | Ir | L-52 | 2 | L-231 | 1 |
| BD-110 | Ir | L-53 | 3 | — | — |
| BD-111 | Ir | L-53 | 2 | L-231 | 1 |
| BD-112 | Ir | L-54 | 3 | — | — |
| BD-113 | Ir | L-54 | 2 | L-231 | 1 |
| BD-114 | Ir | L-55 | 3 | — | — |
| BD-115 | Ir | L-55 | 2 | L-231 | 1 |
| BD-116 | Ir | L-56 | 3 | — | — |
| BD-117 | Ir | L-56 | 2 | L-231 | 1 |
| BD-118 | Ir | L-57 | 3 | — | — |
| BD-119 | Ir | L-57 | 2 | L-231 | 1 |
| BD-120 | Ir | L-58 | 3 | — | — |
| BD-121 | Ir | L-58 | 2 | L-231 | 1 |
| BD-122 | Ir | L-59 | 3 | — | — |
| BD-123 | Ir | L-59 | 2 | L-231 | 1 |
| BD-124 | Ir | L-60 | 3 | — | — |
| BD-125 | Ir | L-60 | 2 | L-231 | 1 |
| BD-126 | Ir | L-61 | 3 | — | — |
| BD-127 | Ir | L-61 | 2 | L-231 | 1 |
| BD-128 | Ir | L-62 | 3 | — | — |
| BD-129 | Ir | L-62 | 2 | L-231 | 1 |
| BD-130 | Ir | L-63 | 3 | — | — |
| BD-131 | Ir | L-63 | 2 | L-231 | 1 |
| BD-132 | Ir | L-64 | 3 | — | — |
| BD-133 | Ir | L-64 | 2 | L-231 | 1 |
| BD-134 | Ir | L-65 | 3 | — | — |
| BD-135 | Ir | L-65 | 2 | L-231 | 1 |
| BD-136 | Ir | L-66 | 3 | — | — |
| BD-137 | Ir | L-66 | 2 | L-231 | 1 |
| BD-138 | Ir | L-67 | 3 | — | — |
| BD-139 | Ir | L-67 | 2 | L-231 | 1 |
| BD-140 | Ir | L-68 | 3 | — | — |
| BD-141 | Ir | L-68 | 2 | L-231 | 1 |
| BD-142 | Ir | L-69 | 3 | — | — |
| BD-143 | Ir | L-69 | 2 | L-231 | 1 |
| BD-144 | Ir | L-70 | 3 | — | — |
| BD-145 | Ir | L-70 | 2 | L-231 | 1 |
| BD-146 | Ir | L-71 | 3 | — | — |
| BD-147 | Ir | L-71 | 2 | L-231 | 1 |
| BD-148 | Ir | L-72 | 3 | — | — |
| BD-149 | Ir | L-72 | 2 | L-231 | 1 |
| BD-150 | Ir | L-73 | 3 | — | — |
| BD-151 | Ir | L-73 | 2 | L-231 | 1 |
| BD-152 | Ir | L-74 | 3 | — | — |
| BD-153 | Ir | L-74 | 2 | L-231 | 1 |
| BD-154 | Ir | L-75 | 3 | — | — |
| BD-155 | Ir | L-75 | 2 | L-231 | 1 |
| BD-156 | Ir | L-76 | 3 | — | — |
| BD-157 | Ir | L-76 | 2 | L-231 | 1 |
| BD-158 | Ir | L-77 | 3 | — | — |
| BD-159 | Ir | L-77 | 2 | L-231 | 1 |
| BD-160 | Ir | L-78 | 3 | — | — |
| BD-161 | Ir | L-78 | 2 | L-231 | 1 |
| BD-162 | Ir | L-79 | 3 | — | — |
| BD-163 | Ir | L-79 | 2 | L-231 | 1 |
| BD-164 | Ir | L-80 | 3 | — | — |
| BD-165 | Ir | L-80 | 2 | L-231 | 1 |
| BD-166 | Ir | L-81 | 3 | — | — |
| BD-167 | Ir | L-81 | 2 | L-231 | 1 |
| BD-168 | Ir | L-82 | 3 | — | — |
| BD-169 | Ir | L-82 | 2 | L-231 | 1 |
| BD-170 | Ir | L-83 | 3 | — | — |
| BD-171 | Ir | L-83 | 2 | L-231 | 1 |
| BD-172 | Ir | L-84 | 3 | — | — |
| BD-173 | Ir | L-84 | 2 | L-231 | 1 |
| BD-174 | Ir | L-85 | 3 | — | — |
| BD-175 | Ir | L-85 | 2 | L-231 | 1 |
| BD-176 | Ir | L-86 | 3 | — | — |
| BD-177 | Ir | L-86 | 2 | L-231 | 1 |
| BD-178 | Ir | L-87 | 3 | — | — |
| BD-179 | Ir | L-87 | 2 | L-231 | 1 |
| BD-180 | Ir | L-88 | 3 | — | — |
| BD-181 | Ir | L-88 | 2 | L-231 | 1 |
| BD-182 | Ir | L-89 | 3 | — | — |
| BD-183 | Ir | L-89 | 3 | L-231 | 1 |
| BD-184 | Ir | L-90 | 3 | — | — |
| BD-185 | Ir | L-90 | 2 | L-231 | 1 |
| BD-186 | Ir | L-91 | 3 | — | — |
| BD-187 | Ir | L-91 | 2 | L-231 | 1 |
| BD-188 | Ir | L-92 | 3 | — | — |
| BD-189 | Ir | L-92 | 2 | L-231 | 1 |
| BD-190 | Ir | L-93 | 3 | — | — |
| BD-191 | Ir | L-93 | 2 | L-231 | 1 |
| BD-192 | Ir | L-94 | 3 | — | — |
| BD-193 | Ir | L-94 | 2 | L-231 | 1 |
| BD-194 | Ir | L-95 | 3 | — | — |
| BD-195 | Ir | L-95 | 2 | L-231 | 1 |
| BD-196 | Ir | L-96 | 3 | — | — |
| BD-197 | Ir | L-96 | 2 | L-231 | 1 |

| Complex | Center Metal | Ligand 1 | Number | Ligand 2 | Number |
|---|---|---|---|---|---|
| BD-198 | Ir | L-97 | 3 | — | — |
| BD-199 | Ir | L-97 | 2 | L-231 | 1 |
| BD-200 | Ir | L-98 | 3 | — | — |
| BD-201 | Ir | L-98 | 2 | L-231 | 1 |
| BD-202 | Ir | L-99 | 3 | — | — |
| BD-203 | Ir | L-99 | 2 | L-231 | 1 |
| BD-204 | Ir | L-100 | 3 | — | — |
| BD-205 | Ir | L-100 | 2 | L-231 | 1 |
| BD-206 | Ir | L-101 | 3 | — | — |
| BD-207 | Ir | L-101 | 2 | L-231 | 1 |
| BD-208 | Ir | L-102 | 3 | — | — |
| BD-209 | Ir | L-102 | 2 | L-231 | 1 |
| BD-210 | Ir | L-103 | 3 | — | — |
| BD-211 | Ir | L-103 | 2 | L-231 | 1 |
| BD-212 | Ir | L-104 | 3 | — | — |
| BD-213 | Ir | L-104 | 2 | L-231 | 1 |
| BD-214 | Ir | L-105 | 3 | — | — |
| BD-215 | Ir | L-105 | 2 | L-231 | 1 |
| BD-216 | Ir | L-106 | 3 | — | — |
| BD-217 | Ir | L-106 | 2 | L-231 | 1 |
| BD-218 | Ir | L-107 | 3 | — | — |
| BD-219 | Ir | L-107 | 2 | L-231 | 1 |
| BD-220 | Ir | L-108 | 3 | — | — |
| BD-221 | Ir | L-108 | 2 | L-231 | 1 |
| BD-222 | Ir | L-109 | 3 | — | — |
| BD-223 | Ir | L-109 | 2 | L-231 | 1 |
| BD-224 | Ir | L-110 | 3 | — | — |
| BD-225 | Ir | L-110 | 2 | L-231 | 1 |
| BD-226 | Ir | L-111 | 3 | — | — |
| BD-227 | Ir | L-111 | 2 | L-231 | 1 |
| BD-228 | Ir | L-112 | 3 | — | — |
| BD-229 | Ir | L-112 | 2 | L-231 | 1 |
| BD-230 | Ir | L-113 | 3 | — | — |
| BD-231 | Ir | L-113 | 2 | L-231 | 1 |
| BD-232 | Ir | L-114 | 3 | — | — |
| BD-233 | Ir | L-114 | 2 | L-231 | 1 |
| BD-234 | Ir | L-115 | 3 | — | — |
| BD-235 | Ir | L-115 | 2 | L-231 | 1 |
| BD-236 | Ir | L-116 | 3 | — | — |
| BD-237 | Ir | L-116 | 2 | L-231 | 1 |
| BD-238 | Ir | L-117 | 3 | — | — |
| BD-239 | Ir | L-117 | 2 | L-231 | 1 |
| BD-240 | Ir | L-118 | 3 | — | — |
| BD-241 | Ir | L-118 | 2 | L-231 | 1 |
| BD-242 | Ir | L-119 | 3 | — | — |
| BD-243 | Ir | L-119 | 2 | L-231 | 1 |
| BD-244 | Ir | L-120 | 3 | — | — |
| BD-245 | Ir | L-120 | 2 | L-231 | 1 |
| BD-246 | Ir | L-121 | 3 | — | — |
| BD-247 | Ir | L-121 | 2 | L-231 | 1 |
| BD-248 | Ir | L-122 | 3 | — | — |
| BD-249 | Ir | L-122 | 2 | L-231 | 1 |
| BD-250 | Ir | L-123 | 3 | — | — |
| BD-251 | Ir | L-123 | 2 | L-231 | 1 |
| BD-252 | Ir | L-124 | 3 | — | — |
| BD-253 | Ir | L-124 | 2 | L-231 | 1 |
| BD-254 | Ir | L-125 | 3 | — | — |
| BD-255 | Ir | L-125 | 2 | L-231 | 1 |
| BD-256 | Ir | L-126 | 3 | — | — |
| BD-257 | Ir | L-126 | 2 | L-231 | 1 |
| BD-258 | Ir | L-127 | 3 | — | — |
| BD-259 | Ir | L-127 | 2 | L-231 | 1 |
| BD-260 | Ir | L-128 | 3 | — | — |
| BD-261 | Ir | L-128 | 2 | L-231 | 1 |
| BD-262 | Ir | L-129 | 3 | — | — |
| BD-263 | Ir | L-129 | 2 | L-231 | 1 |
| BD-264 | Ir | L-130 | 3 | — | — |
| BD-265 | Ir | L-130 | 2 | L-231 | 1 |
| BD-266 | Ir | L-131 | 3 | — | — |
| BD-267 | Ir | L-131 | 2 | L-231 | 1 |
| BD-268 | Ir | L-132 | 3 | — | — |
| BD-269 | Ir | L-132 | 2 | L-231 | 1 |
| BD-270 | Ir | L-133 | 3 | — | — |
| BD-271 | Ir | L-133 | 2 | L-231 | 1 |
| BD-272 | Ir | L-134 | 3 | — | — |
| BD-273 | Ir | L-134 | 2 | L-231 | 1 |
| BD-274 | Ir | L-135 | 3 | — | — |
| BD-275 | Ir | L-135 | 2 | L-231 | 1 |
| BD-276 | Ir | L-136 | 3 | — | — |
| BD-277 | Ir | L-136 | 2 | L-231 | 1 |
| BD-278 | Ir | L-137 | 3 | — | — |
| BD-279 | Ir | L-137 | 2 | L-231 | 1 |
| BD-280 | Ir | L-138 | 3 | — | — |
| BD-281 | Ir | L-138 | 2 | L-231 | 1 |
| BD-282 | Ir | L-139 | 3 | — | — |
| BD-283 | Ir | L-139 | 2 | L-231 | 1 |
| BD-284 | Ir | L-140 | 3 | — | — |
| BD-285 | Ir | L-140 | 2 | L-231 | 1 |
| BD-286 | Ir | L-141 | 3 | — | — |
| BD-287 | Ir | L-141 | 2 | L-231 | 1 |
| BD-288 | Ir | L-142 | 3 | — | — |
| BD-289 | Ir | L-142 | 2 | L-231 | 1 |
| BD-290 | Ir | L-143 | 3 | — | — |
| BD-291 | Ir | L-143 | 2 | L-231 | 1 |
| BD-292 | Ir | L-144 | 3 | — | — |
| BD-293 | Ir | L-144 | 2 | L-231 | 1 |
| BD-294 | Ir | L-145 | 3 | — | — |
| BD-295 | Ir | L-145 | 2 | L-231 | 1 |
| BD-296 | Ir | L-146 | 3 | — | — |
| BD-297 | Ir | L-146 | 2 | L-231 | 1 |
| BD-298 | Ir | L-147 | 3 | — | — |
| BD-299 | Ir | L-147 | 2 | L-231 | 1 |
| BD-300 | Ir | L-148 | 3 | — | — |
| BD-301 | Ir | L-148 | 2 | L-231 | 1 |
| BD-302 | Ir | L-149 | 3 | — | — |
| BD-303 | Ir | L-149 | 2 | L-231 | 1 |
| BD-304 | Ir | L-150 | 3 | — | — |
| BD-305 | Ir | L-150 | 2 | L-231 | 1 |
| BD-306 | Ir | L-151 | 3 | — | — |
| BD-307 | Ir | L-151 | 2 | L-231 | 1 |
| BD-308 | Ir | L-152 | 3 | — | — |
| BD-309 | Ir | L-152 | 2 | L-231 | 1 |
| BD-310 | Ir | L-153 | 3 | — | — |
| BD-311 | Ir | L-153 | 2 | L-231 | 1 |
| BD-312 | Ir | L-154 | 3 | — | — |
| BD-313 | Ir | L-154 | 2 | L-231 | 1 |
| BD-314 | Ir | L-155 | 3 | — | — |
| BD-315 | Ir | L-155 | 2 | L-231 | 1 |
| BD-316 | Ir | L-156 | 3 | — | — |
| BD-317 | Ir | L-156 | 2 | L-231 | 1 |
| BD-318 | Ir | L-157 | 3 | — | — |
| BD-319 | Ir | L-157 | 2 | L-231 | 1 |
| BD-320 | Ir | L-158 | 3 | — | — |
| BD-321 | Ir | L-158 | 2 | L-231 | 1 |
| BD-322 | Ir | L-159 | 3 | — | — |
| BD-323 | Ir | L-159 | 2 | L-231 | 1 |
| BD-324 | Ir | L-160 | 3 | — | — |
| BD-325 | Ir | L-160 | 2 | L-231 | 1 |
| BD-326 | Ir | L-161 | 3 | — | — |
| BD-327 | Ir | L-161 | 2 | L-231 | 1 |
| BD-328 | Ir | L-162 | 3 | — | — |
| BD-329 | Ir | L-162 | 2 | L-231 | 1 |
| BD-330 | Ir | L-163 | 3 | — | — |
| BD-331 | Ir | L-163 | 2 | L-231 | 1 |
| BD-332 | Ir | L-164 | 3 | — | — |
| BD-333 | Ir | L-164 | 2 | L-231 | 1 |
| BD-334 | Ir | L-165 | 3 | — | — |
| BD-335 | Ir | L-165 | 2 | L-231 | 1 |
| BD-336 | Ir | L-166 | 3 | — | — |
| BD-337 | Ir | L-166 | 2 | L-231 | 1 |
| BD-338 | Ir | L-167 | 3 | — | — |
| BD-339 | Ir | L-167 | 2 | L-231 | 1 |
| BD-340 | Ir | L-168 | 3 | — | — |
| BD-341 | Ir | L-168 | 2 | L-231 | 1 |
| BD-342 | Ir | L-169 | 3 | — | — |
| BD-343 | Ir | L-169 | 2 | L-231 | 1 |
| BD-344 | Ir | L-170 | 3 | — | — |
| BD-345 | Ir | L-170 | 2 | L-231 | 1 |
| BD-346 | Ir | L-171 | 3 | — | — |
| BD-347 | Ir | L-171 | 2 | L-231 | 1 |
| BD-348 | Ir | L-172 | 3 | — | — |
| BD-349 | Ir | L-172 | 2 | L-231 | 1 |

-continued

| Complex | Center Metal | Ligand 1 | Number | Ligand 2 | Number |
|---|---|---|---|---|---|
| BD-350 | Ir | L-173 | 3 | — | — |
| BD-351 | Ir | L-173 | 2 | L-231 | 1 |
| BD-352 | Ir | L-174 | 3 | — | — |
| BD-353 | Ir | L-174 | 2 | L-231 | 1 |
| BD-354 | Ir | L-175 | 3 | — | — |
| BD-355 | Ir | L-175 | 2 | L-231 | 1 |
| BD-356 | Ir | L-176 | 3 | — | — |
| BD-357 | Ir | L-176 | 2 | L-231 | 1 |
| BD-358 | Ir | L-177 | 3 | — | — |
| BD-359 | Ir | L-177 | 2 | L-231 | 1 |
| BD-360 | Ir | L-178 | 3 | — | — |
| BD-361 | Ir | L-178 | 2 | L-231 | 1 |
| BD-362 | Ir | L-179 | 3 | — | — |
| BD-363 | Ir | L-179 | 2 | L-231 | 1 |
| BD-364 | Ir | L-180 | 3 | — | — |
| BD-365 | Ir | L-180 | 2 | L-231 | 1 |
| BD-366 | Ir | L-181 | 3 | — | — |
| BD-367 | Ir | L-181 | 2 | L-231 | 1 |
| BD-368 | Ir | L-182 | 3 | — | — |
| BD-369 | Ir | L-182 | 2 | L-231 | 1 |
| BD-370 | Ir | L-183 | 3 | — | — |
| BD-371 | Ir | L-183 | 2 | L-231 | 1 |
| BD-372 | Ir | L-184 | 3 | — | — |
| BD-373 | Ir | L-184 | 2 | L-231 | 1 |
| BD-374 | Ir | L-185 | 3 | — | — |
| BD-375 | Ir | L-185 | 2 | L-231 | 1 |
| BD-376 | Ir | L-186 | 3 | — | — |
| BD-377 | Ir | L-186 | 2 | L-231 | 1 |
| BD-378 | Ir | L-187 | 3 | — | — |
| BD-379 | Ir | L-187 | 2 | L-231 | 1 |
| BD-380 | Ir | L-188 | 3 | — | — |
| BD-381 | Ir | L-188 | 2 | L-231 | 1 |
| BD-382 | Ir | L-189 | 3 | — | — |
| BD-383 | Ir | L-189 | 2 | L-231 | 1 |
| BD-384 | Ir | L-190 | 3 | — | — |
| BD-385 | Ir | L-190 | 2 | L-231 | 1 |
| BD-386 | Ir | L-191 | 3 | — | — |
| BD-387 | Ir | L-191 | 2 | L-231 | 1 |
| BD-388 | Ir | L-192 | 3 | — | — |
| BD-389 | Ir | L-192 | 2 | L-231 | 1 |
| BD-390 | Ir | L-193 | 3 | — | — |
| BD-391 | Ir | L-193 | 2 | L-231 | 1 |
| BD-392 | Ir | L-194 | 3 | — | — |
| BD-393 | Ir | L-194 | 2 | L-231 | 1 |
| BD-394 | Ir | L-195 | 3 | — | — |
| BD-395 | Ir | L-195 | 2 | L-231 | 1 |
| BD-396 | Ir | L-196 | 3 | — | — |
| BD-397 | Ir | L-196 | 2 | L-231 | 1 |
| BD-398 | Ir | L-197 | 3 | — | — |
| BD-399 | Ir | L-197 | 2 | L-231 | 1 |
| BD-400 | Ir | L-198 | 3 | — | — |
| BD-401 | Ir | L-198 | 2 | L-231 | 1 |
| BD-402 | Ir | L-199 | 3 | — | — |
| BD-403 | Ir | L-199 | 2 | L-231 | 1 |
| BD-404 | Ir | L-200 | 3 | — | — |
| BD-405 | Ir | L-200 | 2 | L-231 | 1 |
| BD-406 | Ir | L-201 | 3 | — | — |
| BD-407 | Ir | L-201 | 2 | L-231 | 1 |
| BD-408 | Ir | L-202 | 3 | — | — |
| BD-409 | Ir | L-202 | 2 | L-231 | 1 |
| BD-410 | Ir | L-203 | 3 | — | — |
| BD-411 | Ir | L-203 | 2 | L-231 | 1 |
| BD-412 | Ir | L-204 | 3 | — | — |
| BD-413 | Ir | L-204 | 2 | L-231 | 1 |
| BD-414 | Ir | L-205 | 3 | — | — |
| BD-415 | Ir | L-205 | 2 | L-231 | 1 |
| BD-416 | Ir | L-206 | 3 | — | — |
| BD-417 | Ir | L-206 | 2 | L-231 | 1 |
| BD-418 | Ir | L-207 | 3 | — | — |
| BD-419 | Ir | L-207 | 2 | L-231 | 1 |
| BD-420 | Ir | L-208 | 3 | — | — |
| BD-421 | Ir | L-208 | 2 | L-231 | 1 |
| BD-422 | Ir | L-209 | 3 | — | — |
| BD-423 | Ir | L-209 | 2 | L-231 | 1 |
| BD-424 | Ir | L-210 | 3 | — | — |
| BD-425 | Ir | L-210 | 2 | L-231 | 1 |
| BD-426 | Ir | L-211 | 3 | — | — |
| BD-427 | Ir | L-211 | 2 | L-231 | 1 |
| BD-428 | Ir | L-212 | 3 | — | — |
| BD-429 | Ir | L-212 | 2 | L-231 | 1 |
| BD-430 | Ir | L-213 | 3 | — | — |
| BD-431 | Ir | L-213 | 2 | L-231 | 1 |
| BD-432 | Ir | L-214 | 3 | — | — |
| BD-433 | Ir | L-214 | 2 | L-231 | 1 |
| BD-434 | Ir | L-215 | 3 | — | — |
| BD-435 | Ir | L-215 | 2 | L-231 | 1 |
| BD-436 | Ir | L-216 | 3 | — | — |
| BD-437 | Ir | L-216 | 2 | L-231 | 1 |
| BD-438 | Ir | L-217 | 3 | — | — |
| BD-439 | Ir | L-217 | 2 | L-231 | 1 |
| BD-440 | Ir | L-218 | 3 | — | — |
| BD-441 | Ir | L-218 | 2 | L-231 | 1 |
| BD-442 | Ir | L-219 | 3 | — | — |
| BD-443 | Ir | L-219 | 2 | L-231 | 1 |
| BD-444 | Ir | L-220 | 3 | — | — |
| BD-445 | Ir | L-220 | 2 | L-231 | 1 |
| BD-446 | Ir | L-221 | 3 | — | — |
| BD-447 | Ir | L-221 | 2 | L-231 | 1 |
| BD-448 | Ir | L-222 | 3 | — | — |
| BD-449 | Ir | L-222 | 2 | L-231 | 1 |
| BD-450 | Ir | L-223 | 3 | — | — |
| BD-451 | Ir | L-223 | 2 | L-231 | 1 |
| BD-452 | Ir | L-224 | 3 | — | — |
| BD-453 | Ir | L-224 | 2 | L-231 | 1 |
| BD-454 | Ir | L-225 | 3 | — | — |
| BD-455 | Ir | L-225 | 2 | L-231 | 1 |
| BD-456 | Ir | L-226 | 3 | — | — |
| BD-457 | Ir | L-226 | 2 | L-231 | 1 |
| BD-458 | Ir | L-227 | 3 | — | — |
| BD-459 | Ir | L-227 | 2 | L-231 | 1 |
| BD-460 | Ir | L-228 | 3 | — | — |
| BD-461 | Ir | L-228 | 2 | L-231 | 1 |
| BD-462 | Ir | L-229 | 3 | — | — |
| BD-463 | Ir | L-229 | 2 | L-231 | 1 |
| BD-464 | Ir | L-230 | 3 | — | — |
| BD-465 | Ir | L-230 | 2 | L-231 | 1 |
| BD-466 | Pt | L-2 | 2 | — | — |
| BD-467 | Pt | L-2 | 2 | — | — |
| BD-468 | Pt | L-2 | 1 | L-231 | 1 |
| BD-469 | Pt | L-2 | 1 | L-233 | 1 |
| BD-470 | Pt | L-4 | 2 | — | — |
| BD-471 | Pt | L-4 | 1 | L-231 | 1 |
| BD-472 | Pt | L-9 | 2 | — | — |
| BD-473 | Pt | L-9 | 1 | L-231 | 1 |
| BD-474 | Pt | L-11 | 2 | — | — |
| BD-475 | Pt | L-11 | 1 | L-231 | 1 |
| BD-476 | Pt | L-14 | 2 | — | — |
| BD-477 | Pt | L-14 | 1 | L-231 | 1 |
| BD-478 | Pt | L-15 | 2 | — | — |
| BD-479 | Pt | L-15 | 1 | L-231 | 1 |
| BD-480 | Pt | L-16 | 2 | — | — |
| BD-481 | Pt | L-16 | 1 | L-231 | 1 |
| BD-482 | Pt | L-18 | 2 | — | — |
| BD-483 | Pt | L-20 | 2 | — | — |
| BD-484 | Pt | L-23 | 2 | — | — |
| BD-485 | Pt | L-23 | 1 | L-231 | 1 |
| BD-486 | Pt | L-24 | 2 | — | — |
| BD-487 | Pt | L-24 | 1 | L-231 | 1 |
| BD-488 | Pt | L-26 | 2 | — | — |
| BD-489 | Pt | L-29 | 2 | — | — |
| BD-490 | Pt | L-29 | 1 | L-231 | 1 |
| BD-491 | Pt | L-30 | 1 | L-231 | 1 |
| BD-492 | Pt | L-31 | 2 | — | — |
| BD-493 | Pt | L-31 | 1 | L-231 | 1 |
| BD-494 | Pt | L-32 | 2 | — | — |
| BD-495 | Pt | L-32 | 1 | L-231 | 1 |
| BD-496 | Pt | L-35 | 2 | — | — |
| BD-497 | Pt | L-35 | 1 | L-231 | 1 |
| BD-498 | Pt | L-36 | 2 | — | — |
| BD-499 | Pt | L-36 | 1 | L-231 | 1 |
| BD-500 | Pt | L-37 | 2 | — | — |
| BD-501 | Pt | L-37 | 1 | L-231 | 1 |

| Complex | Center Metal | Ligand 1 | Number | Ligand 2 | Number |
|---|---|---|---|---|---|
| BD-502 | Pt | L-38 | 2 | — | — |
| BD-503 | Pt | L-38 | 1 | L-231 | 1 |
| BD-504 | Pt | L-42 | 2 | — | — |
| BD-505 | Pt | L-42 | 1 | L-231 | 1 |
| BD-506 | Pt | L-43 | 2 | — | — |
| BD-507 | Pt | L-43 | 1 | L-231 | 1 |
| BD-508 | Pt | L-44 | 2 | — | — |
| BD-509 | Pt | L-44 | 1 | L-231 | 1 |
| BD-510 | Pt | L-45 | 2 | — | — |
| BD-511 | Pt | L-45 | 1 | L-231 | 1 |
| BD-512 | Pt | L-46 | 2 | — | — |
| BD-513 | Pt | L-46 | 1 | L-231 | 1 |
| BD-514 | Pt | L-47 | 2 | — | — |
| BD-515 | Pt | L-47 | 1 | L-231 | 1 |
| BD-516 | Pt | L-48 | 2 | — | — |
| BD-517 | Pt | L-48 | 1 | L-231 | 1 |
| BD-518 | Pt | L-48 | 1 | L-232 | 1 |
| BD-519 | Pt | L-48 | 1 | L-233 | 1 |
| BD-520 | Pt | L-48 | 1 | L-234 | 1 |
| BD-521 | Pt | L-49 | 2 | — | — |
| BD-522 | Pt | L-49 | 1 | L-231 | 1 |
| BD-523 | Pt | L-50 | 2 | — | — |
| BD-524 | Pt | L-50 | 1 | L-231 | 1 |
| BD-525 | Pt | L-51 | 2 | — | — |
| BD-526 | Pt | L-51 | 1 | L-231 | 1 |
| BD-527 | Pt | L-52 | 2 | — | — |
| BD-528 | Pt | L-52 | 1 | L-231 | 1 |
| BD-529 | Pt | L-53 | 2 | — | — |
| BD-530 | Pt | L-53 | 1 | L-231 | 1 |
| BD-531 | Pt | L-54 | 2 | — | — |
| BD-532 | Pt | L-54 | 1 | L-231 | 1 |
| BD-533 | Pt | L-55 | 2 | — | — |
| BD-534 | Pt | L-55 | 1 | L-231 | 1 |
| BD-535 | Pt | L-56 | 2 | — | — |
| BD-536 | Pt | L-56 | 1 | L-231 | 1 |
| BD-537 | Pt | L-57 | 2 | — | — |
| BD-538 | Pt | L-57 | 1 | L-231 | 1 |
| BD-539 | Rh | L-2 | 3 | — | — |
| BD-540 | Rh | L-2 | 2 | L-231 | 1 |
| BD-541 | Rh | L-2 | 2 | L-233 | 1 |
| BD-542 | Rh | L-48 | 2 | L-231 | 1 |
| BD-543 | Rh | L-48 | 2 | L-232 | 1 |
| BD-544 | Rh | L-48 | 2 | L-233 | 1 |
| BD-545 | Rh | L-48 | 2 | L-234 | 1 |

| | Ring: Z1 | | | | Ring: Z2 | | | |
|---|---|---|---|---|---|---|---|---|
| | Base | Position of solubilizing | controlling group | | Base | Position of solubilizing | controlling group | |
| Ligand | Skeleton | substituent | Skeleton | Substituent R | Skeleton | substituent | Skeleton | Substituent R |
| L-1 | Z101; $R^8$ = Me | — | — | — | Z201 | 3 | S-1 | R-8 |
| L-2 | Z101; $R^8$ = Me | — | — | — | Z201 | 4 | S-1 | R-1 |
| L-3 | Z101; $R^8$ = Me | — | — | — | Z201 | 4 | S-1 | R-4 |
| L-4 | Z101; $R^8$ = Me | — | — | — | Z201 | 4 | S-1 | R-7 |
| L-5 | Z101; $R^8$ = Me | — | — | — | Z201 | 4 | S-1 | R-8 |
| L-6 | Z101; $R^8$ = Me | — | — | — | Z201 | 4 | S-1 | R-11 |
| L-7 | Z101; $R^8$ = Me | — | — | — | Z201 | 4 | S-1 | R-13 |
| L-8 | Z101; $R^8$ = Me | — | — | — | Z201 | 4 | S-3 | R-6 |
| L-9 | Z101; $R^8$ = Me | — | — | — | Z201 | 4 | S-3 | R-14 |
| L-10 | Z101; $R^8$ = Me | — | — | — | Z201 | 5 | S-1 | R-1 |
| L-11 | Z101; $R^8$ = Ph | — | — | — | Z201 | 4 | S-1 | R-4 |
| L-12 | Z101; $R^8$ = Ph | — | — | — | Z201 | 4 | S-1 | R-7 |
| L-13 | Z101; $R^8$ = Ph | — | — | — | Z201 | 4 | S-1 | R-8 |
| L-14 | Z101; $R^8$ = Ph | — | — | — | Z201 | 4 | S-8 | R-11 |
| L-15 | Z101; $R^8$ = Ph | — | — | — | Z201 | 4 | S-8 | R-13 |
| L-16 | Z101; $R^8$ = Ph | — | — | — | Z201 | 4 | S-23; X = O | R-7 |
| L-17 | Z101; $R^8$ = Ph | — | — | — | Z201 | 4 | S-23; X = CH$_2$ | R-1 |
| L-18 | Z101; $R^8$ = Ph | — | — | — | Z201 | 4 | S-23; X = CH$_2$O | R-1 |
| L-19 | Z101; $R^8$ = Ph | — | — | — | Z201 | 4 | S-24; X = O | R-7 |
| L-20 | Z101; $R^8$ = Ph | — | — | — | Z201 | 4 | S-24; X = CH$_2$ | R-1 |
| L-21 | Z101; $R^8$ = Ph | — | — | — | Z201 | 4 | S-24; X = CH$_2$O | R-1 |
| L-22 | Z101; $R^8$ = Ph | — | — | — | Z201 | 4 | S-25; X = O | R-1 |
| L-23 | Z101; $R^8$ = Ph | — | — | — | Z201 | 4 | S-25; X = CH$_2$ | R-1 |
| L-24 | Z101; $R^8$ = Ph | — | — | — | Z201 | 5 | S-1 | R-1 |
| L-25 | Z101; $R^8$ = Ph | — | — | — | Z201 | 5 | S-1 | R-11 |
| L-26 | Z101; $R^8$ = 2-tolyl | — | — | — | Z201 | 4 | S-18 | R-11 |
| L-27 | Z101; $R^8$ = 2-tolyl | — | — | — | Z201 | 4 | S-1 | R-4 |
| L-28 | Z101; $R^8$ = 2,6-Dimethyl phenyl | — | — | — | Z201 | 4 | S-18 | R-11 |
| L-29 | Z101; $R^8$ = 2,6-Dimethyl phenyl | — | — | — | Z201 | 4 | S-1 | R-4 |
| L-30 | Z101; $R^8$ = Me | — | — | — | Z201 | 5 | S-1 | R-4 |
| L-31 | Z101; $R^8$ = Me | — | — | — | Z201 | 5 | S-1 | R-7 |
| L-32 | Z101; $R^8$ = Me | — | — | — | Z201 | 5 | S-1 | R-8 |
| L-33 | Z101; $R^8$ = Me | — | — | — | Z201 | 5 | S-1 | R-11 |
| L-34 | Z101; $R^8$ = Me | — | — | — | Z201 | 5 | S-1 | R-13 |
| L-35 | Z101; $R^8$ = Me | — | — | — | Z201 | 6 | S-1 | R-8 |
| L-36 | Z101; $R^8$ = Me | — | — | — | Z201 | 4 | S-2 | R-8 |

-continued

| | | | | | | | | |
|---|---|---|---|---|---|---|---|---|
| L-37 | Z101; R$^8$ = Me | — | — | — | Z201 | 4 | S-3 | R-8 |
| L-38 | Z101; R$^8$ = Me | — | — | — | Z201 | 3, 5 | S-1 | R-1 |
| L-39 | Z101; R$^8$ = Me | — | — | — | Z201 | 4 | S-4 | R-8 |
| L-40 | Z101; R$^8$ = Me | — | — | — | Z201 | 4 | S-5 | R-8 |
| L-41 | Z101; R$^8$ = Me | — | — | — | Z201 | 4 | S-6 | R-8 |
| L-42 | Z101; R$^8$ = Me | — | — | — | Z201 | 4 | S-7 | R-8 |
| L-43 | Z101; R$^8$ = Me | — | — | — | Z201 | 4 | S-8 | R-8 |
| L-44 | Z101; R$^8$ = Me | — | — | — | Z201 | 4 | S-10 | R-8 |
| L-45 | Z101; R$^8$ = Me | — | — | — | Z201 | 4 | S-11 | R-8 |
| L-46 | Z101; R$^8$ = Me | — | — | — | Z201 | 4 | S-18 | R-8 |
| L-47 | Z101; R$^8$ = Me | — | — | — | Z201 | 5 | S-18 | R-8 |
| L-48 | Z101; R$^8$ = Me | — | — | — | Z201 | 4 | S-18 | R-11 |
| L-49 | Z101; R$^8$ = Me | — | — | — | Z201 | 4 | S-18 | R-12 |
| L-50 | Z101; R$^8$ = Me | — | — | — | Z201 | 5 | S-18 | R-11 |
| L-51 | Z101; R$^8$ = Me | — | — | — | Z201 | 5 | S-18 | R-13 |
| L-52 | Z101; R$^8$ = Me | — | — | — | Z201 | 4 | S-19 | R-7 |
| L-53 | Z101; R$^8$ = Me | — | — | — | Z201 | 4 | S-20 | R-1 |
| L-54 | Z101; R$^8$ = Me | — | — | — | Z201 | 4 | S-20 | R-6 |
| L-55 | Z101; R$^8$ = Me | — | — | — | Z201 | 4 | S-21 | R-7 |
| L-56 | Z101; R$^8$ = Me | — | — | — | Z201 | 4 | S-21 | R-8 |
| L-57 | Z101; R$^8$ = Me | — | — | — | Z201 | 4 | S-22 | R-7 |
| L-58 | Z101; R$^8$ = Me | — | — | — | Z202 | 4 | S-1 | R-4 |
| L-59 | Z101; R$^8$ = Me | — | — | — | Z202 | 4 | S-1 | R-7 |
| L-60 | Z101; R$^8$ = Me | — | — | — | Z202 | 4 | S-1 | R-8 |
| L-61 | Z101; R$^8$ = Me | — | — | — | Z202 | R$^8$ | S-1 | R-11 |
| L-62 | Z101; R$^8$ = Me | — | — | — | Z202 | R$^8$ | S-1 | R-13 |
| L-63 | Z101; R$^8$ = Me | — | — | — | Z202 | R$^8$ | S-9 | R-7 |
| L-64 | Z101; R$^8$ = Me | — | — | — | Z202 | R$^8$ | S-12 | R-7 |
| L-65 | Z101; R$^8$ = Me | — | — | — | Z202 | R$^8$ | S-13 | R-1 |
| L-66 | Z101; R$^8$ = Me | — | — | — | Z202 | R$^8$ | S-14 | R-7 |
| L-67 | Z101; R$^8$ = Me | — | — | — | Z202 | R$^8$ | S-16 | R-7 |
| L-68 | Z101; R$^8$ = Me | — | — | — | Z202 | R$^8$ | S-17 | R-1 |
| L-69 | Z101; R$^8$ = Me | — | — | — | Z202 | R$^8$ | S-18 | R-8 |
| L-70 | Z101; R$^8$ = Me | — | — | — | Z202 | R$^8$ | S-18 | R-11 |
| L-71 | Z101; R$^8$ = Me | — | — | — | Z203 | R$^8$ = Ph, 4 | S-1 | R-4 |
| L-72 | Z101; R$^8$ = Me | — | — | — | Z206 | 4 | S-1 | R-4 |
| L-73 | Z101; R$^8$ = Me | — | — | — | Z206 | 4 | S-1 | R-7 |
| L-74 | Z101; R$^8$ = Me | — | — | — | Z206 | 4 | S-1 | R-8 |
| L-75 | Z101; R$^8$ = Me | — | — | — | Z206 | 4 | S-1 | R-11 |
| L-76 | Z101; R$^8$ = Me | — | — | — | Z206 | 4 | S-1 | R-13 |
| L-77 | Z101; R$^8$ = Me | — | — | — | Z206 | 4 | S-18 | R-8 |
| L-78 | Z101; R$^8$ = Me | — | — | — | Z206 | 4 | S-18 | R-11 |
| L-79 | Z101; R$^8$ = Me | — | — | — | Z212 | 5 | S-1 | R-4 |
| L-80 | Z101; R$^8$ = Me | — | — | — | Z212 | 5 | S-1 | R-7 |
| L-81 | Z101; R$^8$ = Me | — | — | — | Z212 | 5 | S-1 | R-8 |
| L-82 | Z101; R$^8$ = Me | — | — | — | Z212 | 5 | S-1 | R-11 |
| L-83 | Z101; R$^8$ = Me | — | — | — | Z212 | 5 | S-1 | R-13 |
| L-84 | Z101; R$^8$ = Me | — | — | — | Z212 | 5 | S-18 | R-8 |
| L-85 | Z101; R$^8$ = Me | — | — | — | Z212 | 5 | S-18 | R-11 |
| L-86 | Z101; R$^8$ = Me | — | — | — | Z217 | 4 | S-15 | R-7 |
| L-87 | Z101; R$^8$ = Me | 4 | S-1 | R-1 | Z201 | 4 | S-1 | R-1 |
| L-88 | Z101; R$^8$ = Me | 4 | S-1 | R-1 | Z201 | 4 | S-18 | R-11 |
| L-89 | Z101; R$^8$ = Me | 4 | S-18 | R-8 | Z201 | 4 | S-18 | R-8 |
| L-90 | Z101; R$^8$ = Me | 4 | S-18 | R-11 | Z201 | 4 | S-18 | R-11 |
| L-91 | Z101 | R$^8$ | S-1 | R-2 | Z201 | — | — | — |
| L-92 | Z101 | R$^8$ | S-1 | R-2 | Z201 | 4 | S-18 | R-11 |
| L-93 | Z101 | R$^8$ | S-1 | R-3 | Z201 | — | — | — |
| L-94 | Z101 | R$^8$ | S-1 | R-4 | Z201 | — | — | — |
| L-95 | Z101 | R$^8$ | S-1 | R-5 | Z201 | — | — | — |
| L-96 | Z102 | R$^8$ | S-2 | R-1 | Z201 | 4 | S-1 | R-1 |
| L-97 | Z102 | R$^8$ | S-2 | R-1 | Z201 | 4 | S-18 | R-11 |
| L-98 | Z102; R$^8$ = Me | — | — | — | Z201 | 4 | S-18 | R-11 |
| L-99 | Z103 | R$^8$ | S-2 | R-1 | Z201 | 4 | S-1 | R-1 |
| L-100 | Z103 | R$^8$ | S-18 | R-11 | Z201 | 4 | S-1 | R-1 |
| L-101 | Z103 | R$^8$ | S-18 | R-11 | Z201 | 4 | S-1 | R-1 |
| L-102 | Z104; R$^8$ = Me | — | — | — | Z201 | 4 | S-18 | R-11 |
| L-103 | Z105 | 4 | S-2 | R-1 | Z201 | 4 | S-1 | R-1 |
| L-104 | Z105 | — | — | — | Z201 | 4 | S-18 | R-11 |
| L-105 | Z105 | 4 | S-2 | R-1 | Z201 | 4 | S-18 | R-11 |
| L-106 | Z106 | — | — | — | Z204 | 4 | S-18 | R-11 |
| L-107 | Z107 | 4 | S-18 | R-11 | Z201 | — | — | — |
| L-108 | Z107 | 4 | S-18 | R-11 | Z201 | — | — | — |
| L-109 | Z107 | 4 | S-18 | R-11 | Z201 | 4 | S-1 | R-1 |
| L-110 | Z107 | 4 | S-18 | R-11 | Z201 | 4 | S-18 | R-11 |
| L-111 | Z107 | 4 | S-18 | R-11 | Z208 | — | — | — |
| L-112 | Z108 | 4 | S-2 | R-1 | Z201 | 4 | S-1 | R-1 |
| L-113 | Z108 | — | — | — | Z201 | 4 | S-18 | R-11 |
| L-114 | Z108 | 4 | S-2 | R-1 | Z201 | 4 | S-18 | R-11 |
| L-115 | Z108 | 4 | S-18 | R-11 | Z217 | — | — | — |

| | | | | | | | | |
|---|---|---|---|---|---|---|---|---|
| L-116 | Z109 | 4 | S-18 | R-11 | Z201 | — | — | — |
| L-117 | Z109 | 4 | S-18 | R-11 | Z201 | — | — | — |
| L-118 | Z109 | 4 | S-18 | R-11 | Z201 | 4 | S-1 | R-1 |
| L-119 | Z109 | 4 | S-18 | R-11 | Z201 | 4 | S-18 | R-11 |
| L-120 | Z109 | 4 | S-18 | R-11 | Z216 | — | — | — |
| L-121 | Z109 | 4 | S-18 | R-11 | Z217 | — | — | — |
| L-122 | Z110 | 4 | S-2 | R-1 | Z201 | 4 | S-18 | R-11 |
| L-123 | Z111 | — | — | — | Z201 | 4 | S-18 | R-11 |
| L-124 | Z111 | 4 | S-18 | R-11 | Z201 | 4 | S-18 | R-11 |
| L-125 | Z111 | 4 | S-18 | R-11 | Z205 | — | — | — |
| L-126 | Z112 | — | — | — | Z201 | 4 | S-18 | R-11 |
| L-127 | Z113; $R^8$ = Me | — | — | — | Z201 | 4 | S-1 | R-1 |
| L-128 | Z113; $R^8$ = Me | — | — | — | Z201 | 4 | S-18 | R-11 |
| L-129 | Z113; $R^8$ = Me | — | — | — | Z201 | 4 | S-1 | R-1 |
| L-130 | Z113 | $R^8$ | S-2 | R-1 | Z201 | 4 | S-1 | R-1 |
| L-131 | Z113 | $R^8$ | S-2 | R-1 | Z201 | 4 | S-18 | R-11 |
| L-132 | Z113 | $R^8$ | S-18 | R-11 | Z201 | 4 | S-1 | R-1 |
| L-133 | Z113 | $R^8$ | S-18 | R-11 | Z207 | — | — | — |
| L-134 | Z113 | $R^8$ | S-18 | R-11 | Z208 | — | — | — |
| L-135 | Z113 | $R^8$ | S-18 | R-11 | Z209 | — | — | — |
| L-136 | Z113 | $R^8$ | S-18 | R-11 | Z214 | — | — | — |
| L-137 | Z113 | $R^8$ | S-18 | R-11 | Z215 | — | — | — |
| L-138 | Z114; $R^8$ = Me | — | — | — | Z201 | 4 | S-1 | R-1 |
| L-139 | Z114; $R^8$ = Me | — | — | — | Z201 | 4 | S-18 | R-11 |
| L-140 | Z114; $R^8$ = Me | — | — | — | Z201 | 4 | S-1 | R-1 |
| L-141 | Z114 | $R^8$ | S-2 | R-1 | Z201 | 4 | S-1 | R-1 |
| L-142 | Z114 | $R^8$ | S-2 | R-1 | Z201 | 4 | S-18 | R-11 |
| L-143 | Z114 | $R^8$ | S-18 | R-11 | Z201 | 4 | S-1 | R-1 |
| L-144 | Z115; $R^8$ = Me | — | — | — | Z201 | 4 | S-1 | R-1 |
| L-145 | Z115; $R^8$ = Me | — | — | — | Z201 | 4 | S-18 | R-11 |
| L-146 | Z115; $R^8$ = Me | — | — | — | Z201 | 4 | S-1 | R-1 |
| L-147 | Z115 | $R^8$ | S-2 | R-1 | Z201 | 4 | S-1 | R-1 |
| L-148 | Z115 | $R^8$ | S-2 | R-1 | Z201 | 4 | S-18 | R-11 |
| L-149 | Z115 | $R^8$ | S-18 | R-11 | Z201 | 4 | S-1 | R-1 |
| L-150 | Z116; $R^8$ = Me | — | — | — | Z201 | 4 | S-1 | R-1 |
| L-151 | Z116; $R^8$ = Me | — | — | — | Z201 | 4 | S-18 | R-11 |
| L-152 | Z116; $R^8$ = Me | — | — | — | Z201 | 4 | S-1 | R-1 |
| L-153 | Z117 | — | — | — | Z201 | 4 | S-1 | R-1 |
| L-154 | Z117 | — | — | — | Z201 | 4 | S-18 | R-11 |
| L-155 | Z117 | — | — | — | Z201 | 4 | S-1 | R-1 |
| L-156 | Z118 | — | — | — | Z201 | 4 | S-1 | R-1 |
| L-157 | Z118 | — | — | — | Z201 | 4 | S-18 | R-11 |
| L-158 | Z118 | — | — | — | Z201 | 4 | S-1 | R-1 |
| L-159 | Z119 | — | — | — | Z201 | 4 | S-1 | R-1 |
| L-160 | Z119 | — | — | — | Z201 | 4 | S-18 | R-11 |
| L-161 | Z119 | — | — | — | Z201 | 4 | S-1 | R-1 |
| L-162 | Z120 | — | — | — | Z201 | 4 | S-18 | R-11 |
| L-163 | Z121 | — | — | — | Z201 | 4 | S-18 | R-11 |
| L-164 | Z122 | — | — | — | Z201 | 4 | S-18 | R-11 |
| L-165 | Z123 | — | — | — | Z201 | 4 | S-18 | R-11 |
| L-166 | Z124 | — | — | — | Z201 | 4 | S-18 | R-11 |
| L-167 | Z125; $R^8$ = Me | — | — | — | Z201 | 4 | S-1 | R-1 |
| L-168 | Z125; $R^8$ = Me | — | — | — | Z201 | 4 | S-18 | R-11 |
| L-169 | Z125; $R^8$ = Me | — | — | — | Z201 | 4 | S-1 | R-1 |
| L-170 | Z125 | $R^8$ | S-2 | R-1 | Z201 | 4 | S-1 | R-1 |
| L-171 | Z125 | $R^8$ | S-2 | R-1 | Z201 | 4 | S-18 | R-11 |
| L-172 | Z125 | $R^8$ | S-18 | R-11 | Z201 | 4 | S-1 | R-1 |
| L-173 | Z125; $R^8$ = Me | 4 | S-18 | R-11 | Z206 | — | — | — |
| L-174 | Z125; $R^8$ = Me | 4 | S-18 | R-11 | Z207 | — | — | — |
| L-175 | Z125; $R^8$ = Me | 4 | S-18 | R-11 | Z208 | — | — | — |
| L-176 | Z125; $R^8$ = Me | 4 | S-18 | R-11 | Z209 | — | — | — |
| L-177 | Z125; $R^8$ = Me | 4 | S-18 | R-11 | Z210 | — | — | — |
| L-178 | Z125; $R^8$ = Me | 4 | S-18 | R-11 | Z211 | — | — | — |
| L-179 | Z125; $R^8$ = Me | 4 | S-18 | R-11 | Z212 | — | — | — |
| L-180 | Z125; $R^8$ = Me | 4 | S-18 | R-11 | Z213 | — | — | — |
| L-181 | Z125; $R^8$ = Me | — | — | — | Z201 | 4 | S-18 | R-11 |
| L-182 | Z125; $R^8$ = H | — | — | — | Z201 | 4 | S-18 | R-11 |
| L-183 | Z126; $R^8$ = Me | — | — | — | Z201 | 4 | S-18 | R-11 |
| L-184 | Z127; $R^8$ = Me | — | — | — | Z201 | 4 | S-18 | R-11 |
| L-185 | Z128; $R^8$ = Me | — | — | — | Z201 | 4 | S-18 | R-11 |
| L-186 | Z129 | — | — | — | Z201 | 4 | S-18 | R-11 |
| L-187 | Z130 | — | — | — | Z201 | 4 | S-18 | R-11 |
| L-188 | Z131 | — | — | — | Z201 | 4 | S-18 | R-11 |
| L-189 | Z132 | — | — | — | Z201 | 4 | S-18 | R-11 |
| L-190 | Z133 | 4 | S-18 | R-11 | Z201 | — | — | — |
| L-191 | Z133 | 4 | S-18 | R-11 | Z201 | 4 | S-1 | R-1 |
| L-192 | Z133 | 4 | S-18 | R-11 | Z201 | 4 | S-18 | R-11 |
| L-193 | Z134 | — | — | — | Z201 | 4 | S-18 | R-11 |
| L-194 | Z135 | — | — | — | Z201 | 4 | S-18 | R-11 |

-continued

| | | | | | | | | |
|---|---|---|---|---|---|---|---|---|
| L-195 | Z136 | — | — | — | Z201 | 4 | S-18 | R-11 |
| L-196 | Z137 | 4 | S-18 | R-11 | Z201 | — | — | — |
| L-197 | Z137 | 4 | S-18 | R-11 | Z201 | 4 | S-1 | R-1 |
| L-198 | Z137 | 4 | S-18 | R-11 | Z201 | 4 | S-18 | R-11 |
| L-199 | Z137 | — | — | — | Z201 | 4 | S-18 | R-11 |
| L-200 | Z138 | — | — | — | Z201 | 4 | S-18 | R-11 |
| L-201 | Z139 | — | — | — | Z201 | 4 | S-18 | R-11 |
| L-202 | Z140 | — | — | — | Z201 | 4 | S-18 | R-11 |
| L-203 | Z141 | 4 | S-18 | R-11 | Z201 | — | — | — |
| L-204 | Z141 | 4 | S-18 | R-11 | Z201 | 4 | S-1 | R-1 |
| L-205 | Z141 | 4 | S-18 | R-11 | Z201 | 4 | S-18 | R-11 |
| L-206 | Z141 | — | — | — | Z201 | 4 | S-18 | R-11 |
| L-207 | Z142 | 4 | S-18 | R-11 | Z201 | — | — | — |
| L-208 | Z142 | 4 | S-18 | R-11 | Z201 | 4 | S-1 | R-1 |
| L-209 | Z142 | 4 | S-18 | R-11 | Z201 | 4 | S-18 | R-11 |
| L-210 | Z142 | — | — | — | Z201 | 4 | S-18 | R-11 |
| L-211 | Z143 | — | — | — | Z201 | 4 | S-18 | R-11 |
| L-212 | Z144 | — | — | — | Z201 | 4 | S-18 | R-11 |
| L-213 | Z145; $R^9$ = Me, $R^{10}$ = H, $R^{11}$ = H | — | — | — | Z201 | 4 | S-1 | R-1 |
| L-214 | Z145; $R^9$ = Me, $R^{10}$ = H, $R^{11}$ = H | — | — | — | Z201 | 4 | S-18 | R-11 |
| L-215 | Z145; $R^9$ = Me, $R^{10}$ = H, $R^{11}$ = H | — | — | — | Z201 | 4 | S-25; X = O | R-11 |
| L-216 | Z145; $R^9$ = Ph, $R^{10}$ = H, $R^{11}$ = H | — | — | — | Z201 | 4 | S-1 | R-1 |
| L-217 | Z145; $R^9$ = Ph, $R^{10}$ = H, $R^{11}$ = H | — | — | — | Z201 | 4 | S-18 | R-11 |
| L-218 | Z145; $R^2$ = 2,6-Dimethyl phenyl, $R^{10}$ = H, $R^{11}$ = H | — | — | — | Z201 | 4 | S-1 | R-1 |
| L-219 | Z145; $R^2$ = 2,6-Dimethyl phenyl, $R^{10}$ = H, $R^{11}$ = H | — | — | — | Z201 | 4 | S-18 | R-11 |
| L-220 | Z145; $R^{10}$ = H, $R^{11}$ = H | $R^9$ | S-1 | R-4 | Z201 | — | — | — |
| L-221 | Z145; $R^{10}$ = H, $R^{11}$ = H | $R^9$ | S-1 | R-4 | Z201 | 4 | S-18 | R-11 |
| L-222 | Z145; $R^{10}$ = H, $R^{11}$ = H | $R^9$ | S-1 | R-4 | Z218; X = O | — | — | — |
| L-223 | Z145; $R^{10}$ = H, $R^{11}$ = H | $R^9$ | S-1 | R-4 | Z218; X = N-Et | — | — | — |
| L-224 | Z145; $R^{10}$ = H, $R^{11}$ = H | $R^9$ | S-1 | R-4 | Z218; X = C(n-Oct)$_2$ | — | — | — |
| L-225 | Z145; $R^{10}$ = H, $R^{11}$ = H | $R^9$ | — | R-4 | Z218; X = C(n-Oct)$_2$ | — | — | — |
| L-226 | Z145; $R^{10}$ = H, $R^{11}$ = H | $R^9$ | — | R-4 | Z218; X = C(n-Oct)$_2$ | — | — | — |
| L-227 | Z145; $R^9$ = Me, $R^{11}$ = H | $R^{10}$ | — | R-4 | Z218; X = C(n-Oct)$_2$ | — | — | — |
| L-228 | Z145; $R^9$ = 2,6-Dimethyl phenyl, $R^{11}$ = H | $R^{10}$ | — | R-4 | Z218; X = C(n-Oct)$_2$ | — | — | — |
| L-229 | Z145; $R^9$ = Me, $R^{10}$ = H | $R^{11}$ | — | R-4 | Z218; X = C(n-Oct)$_2$ | — | — | — |
| L-230 | Z145; $R^9$ = Ph, $R^{10}$ = H | $R^{11}$ | — | R-4 | Z218; X = C(n-Oct)$_2$ | — | — | — |

Z1

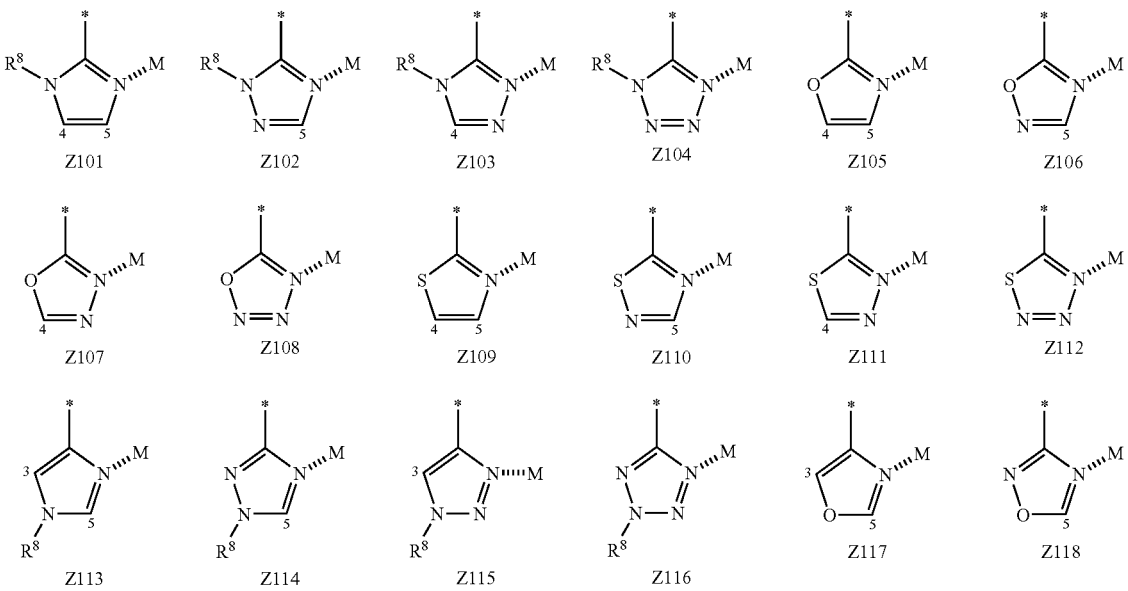

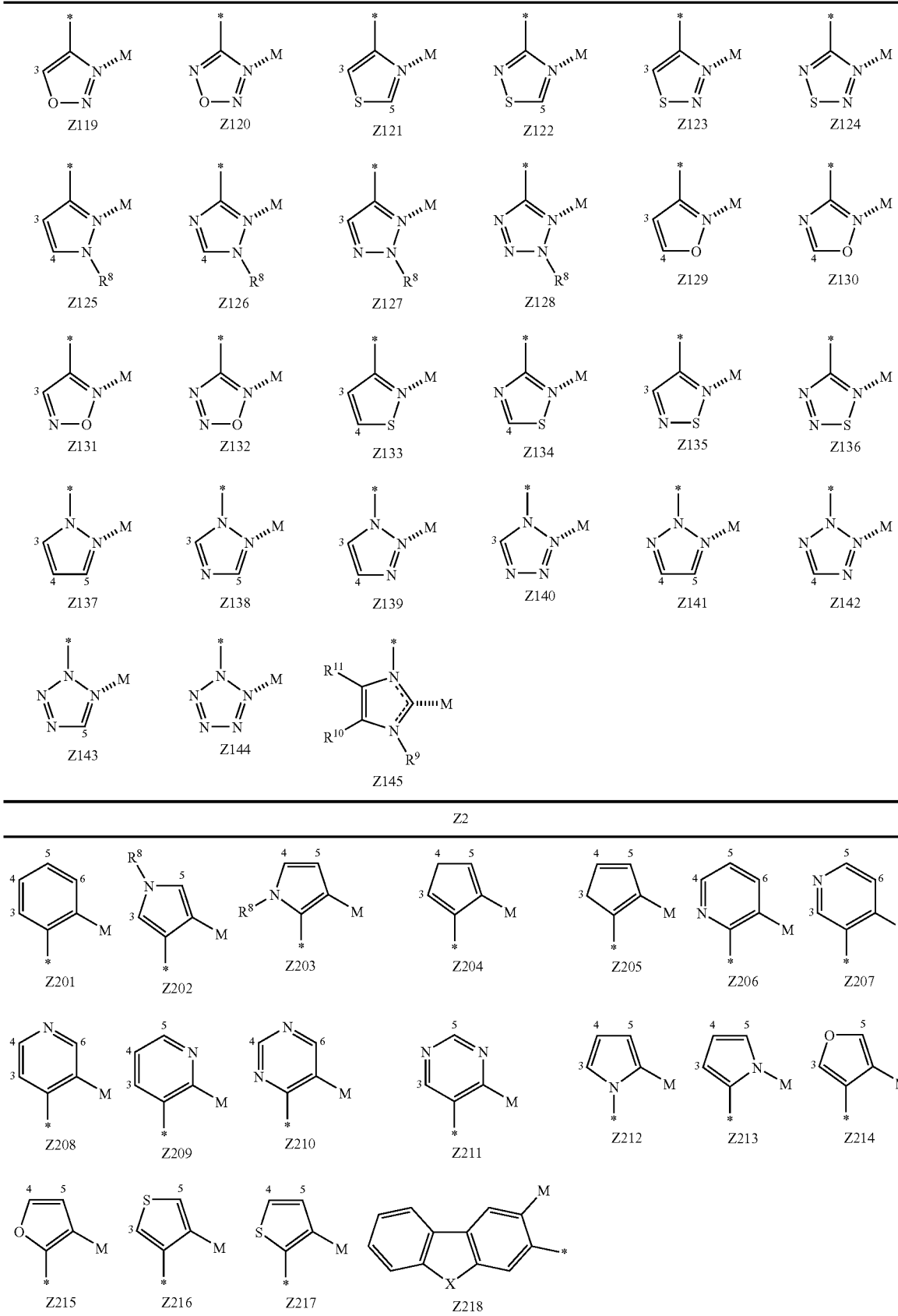

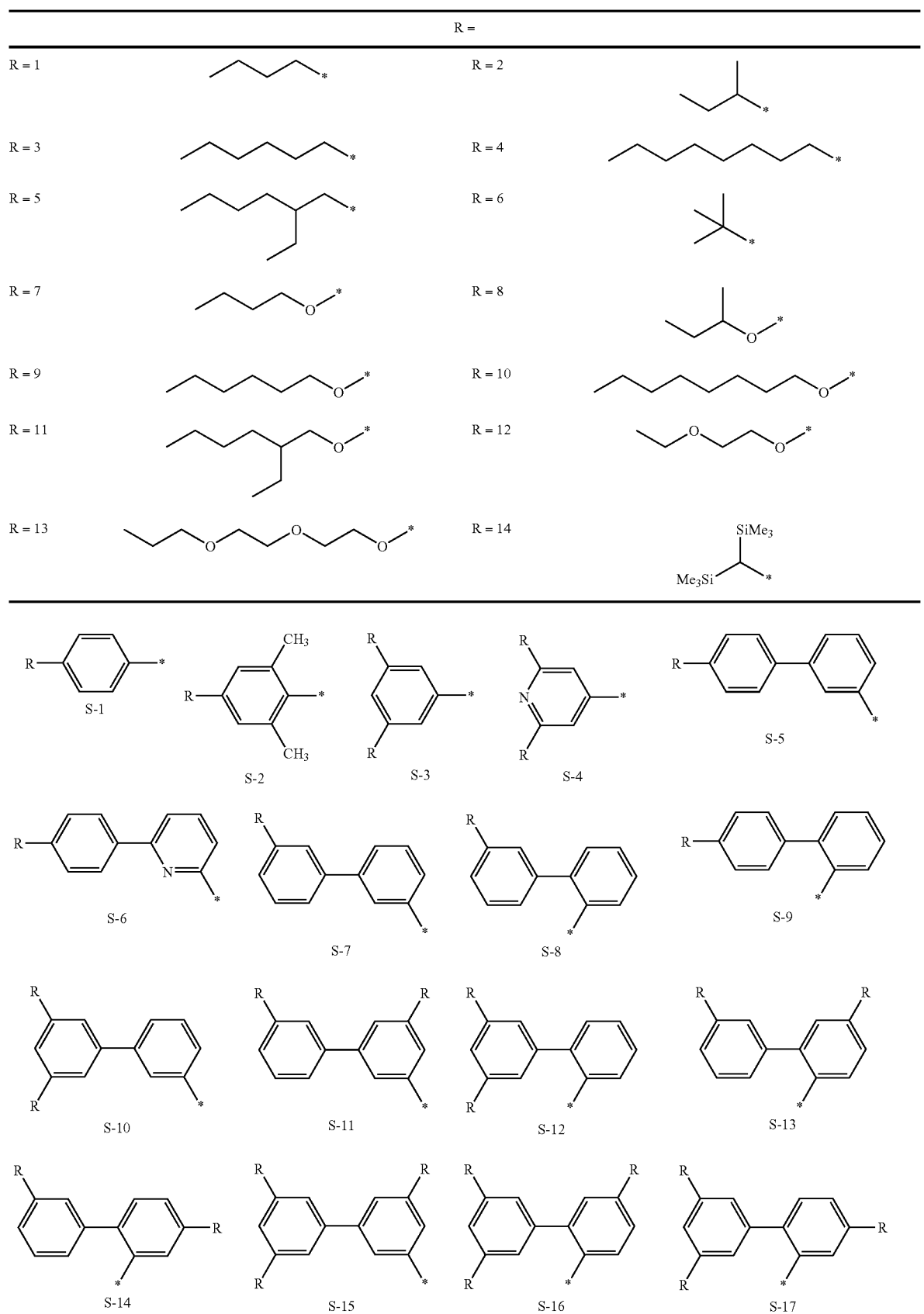

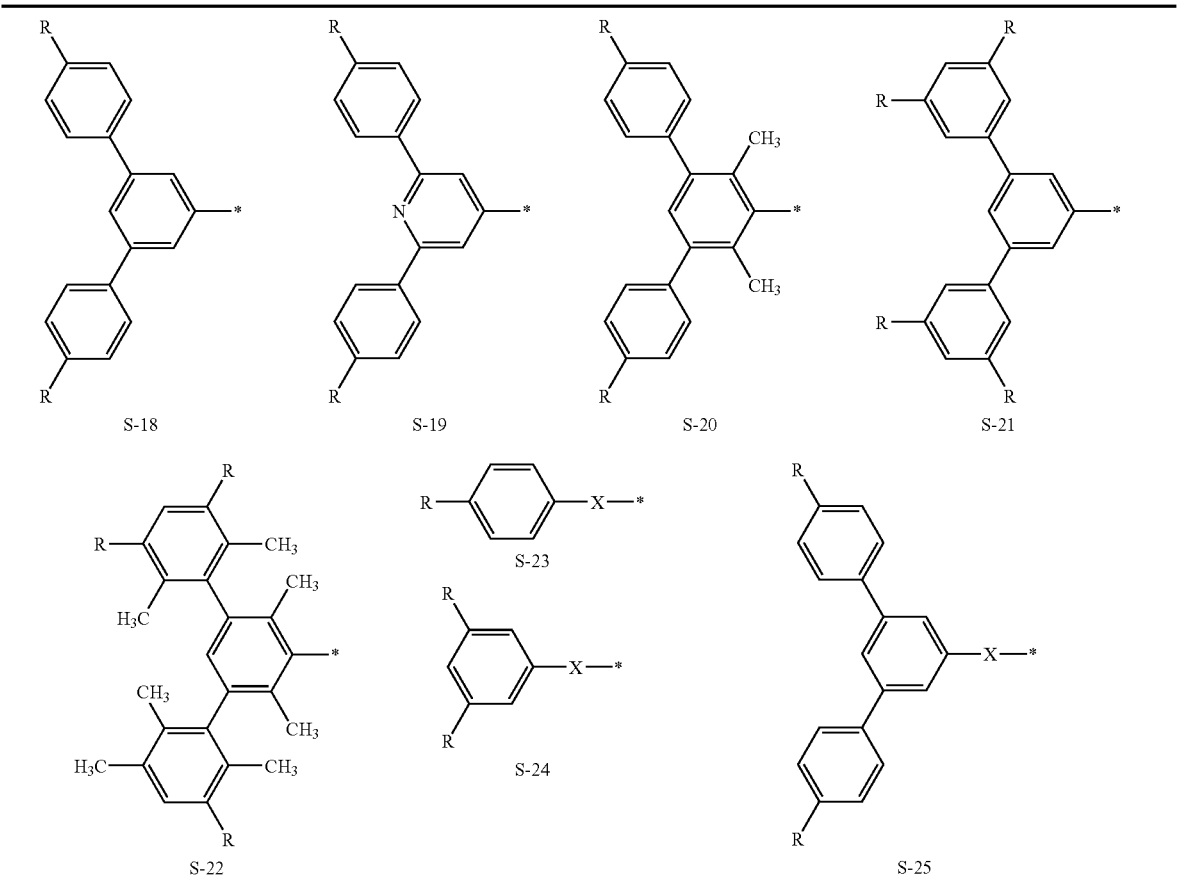

In the above list, X in Z218, S-23, S-24 and S-25 is O, N, S or C(R)$_2$, respectively, wherein R is a hydrogen atom or an alky or aromatic hydrocarbon group which may have a substituent.

An example of a S-member aromatic heterocycle represented by Z1 in the Formula (1) includes Z101 to Z145, wherein N . . . M represents that a coordinate bond is formed between a nitrogen atom N and M (Ir or Pt) forming the 5-member aromatic heterocycle.

An example of a cyclopentadiene, 6-member aromatic hydrocarbon ring, and 5 or 6-member aromatic heterocycle represented by Z2 in any one of the Formulas (11 to (8) includes Z1201 to Z1218, wherein −M represents that M (Ir or Pt) bonds to a ring structure formed by Z2.

An asterisk (*) in each structure of Z101 to 145, and Z201 to 218 represents a position that rings represented by Z1 and Z2 bond through the asterisk (*).

Structural layer of the organic EL element of the invention is described. Preferable concrete examples of the layer constitution of the organic EL element of the invention are listed below, though the invention is not limited to them.

(1) Anode/Light emission layer/Electron transfer layer/Cathode (2) Anode/Positive hole transfer layer/Light emission layer/Electron transfer layer/Cathode (3) Anode/Positive hole transfer layer/Light emission layer/Positive hole blocking layer/Electron transfer layer/Cathode (4) Anode/Positive hole transfer layer/Light emission layer/Positive hole blocking layer/Electron transfer layer/Cathode buffer layer/Cathode (5) Anode/Anode buffer layer/Positive hole transfer layer/Light emission layer/Positive hole blocking layer/Electron transfer layer/Cathode buffer layer/Cathode The maximum wave length of the emission of the blue emission, layer is preferably 430-480 nm, the maximum wave length of the emission of the green emission layer is preferably 510-550 nm, and maximum wave length of the emission of the red emission layer is preferably 600-640 nm in the organic EL element of this invention. The display apparatus preferably employs this organic EL element. A white emission layer may be composed by superposing at least these three emission layers. The organic EL element may comprise a non-emission intermediate layer between the emission layers. The organic EL element is preferably a white emission layer, and a display element employing this.

Layers composing the organic EL element of this invention will be described.

<<Light Emission Layer>>

The light emission layer relating to the invention is a layer in which electrons and positive holes each injected from the electrodes or the electron transfer layer and the positive hole transfer layer, respectively, are recombined to emit light and the portion of light emission may be inside of the layer or the interface of the light emission layer and the adjacent layer.

The total thickness of the light emission layer is not specifically restricted but preferably within the range of from 2 nm to 5 μm, more preferably from 2 nm to 200 nm, and particularly preferably from 10 nm to 20 nm in view of uniformity of the layer, preventing the application of unnecessary high voltage at the light emission and improving stability of emission color against driving current.

The light emission layer can be prepared by forming a layer of the later-mentioned light emission dopant and the host compound by known method such as a vacuum deposition method, spin coating method, LB method and ink-jet method.

The emission layer of the organic EL element of this invention preferably contains an emission compound and at least one of light emission dopant, that is, a phosphorescent dopant (a phosphorescent light emission dopant) or a fluorescent dopant (a fluorescent light emission dopant) Host Compound (Emission Host)

The host compound used in this invention will be described.

As the host compound to be contained in the light emission layer of the organic EL element, a compound is defined as a compound having a weight ratio of the host compound in the compounds contained in the light emission layer is not less than 20%, and having a phosphorescent quantum efficiency of the fluorescent light emission of less than 0.1 and more preferably less than 0.01 at room temperature (25° C.). The weight ratio of the host compound in the compounds contained in the light emission layer is preferably not less than 20%.

As the host compound, known host compounds may be used singly or in a combination of plural kinds thereof. The transfer of charge can be controlled by the combination use of the host compounds so as to raise the efficiency of the organic EL element. Moreover, mixing of different emitted light is made possible by the use of plural kinds of light emission material so as that optional color light can be obtained.

The light emission host compound used in this invention may be a known low molecular weight compound, a polymer compound having a repeating unit or a low molecular compound having a polymerizable group such as a vinyl group and an epoxy group (vapor deposition polymerizable light emission host).

As the known host compound, a compound is preferable which has positive hole transport ability and electron transport ability, an ability to prevent shift of emitted light to loner wavelength side and high glass transition point Tg.

As known examples of an emission host, compounds described in the following Documents are preferable:

For example, JP-A 2001-257076, JP-A 2002-308855, JP-A 2001-313179, JP-A 2002-319491, JP-A 2001-357977, JP-A 2002-334786, JP-A 2002-8860, JP-A 2002-334787, JP-A 2002-15871, JP-A 2002-334788, JP-A 2002-43056, JP-A 2002-334789, JP-A 2002-75645, JP-A 2002-338579, JP-A 2002-105445, JP-A 2002-343568, JP-A 2002-141173, JP-A 2002-352957, JP-A 2002-203683, JP-A 2002-363227, JP-A 2002-231453, JP-A 2003-3165, JP-A 2002-234888, JP-A 2003-27048, JP-A 2002-255934, JP-A 2002-260861, JP-A 2002-280183, JP-A 2002-299060, JP-A 2002-302516, JP-A 2002-305083, JP-A 2002-305084 and JP-A 2002-308837.

Emission Dopant

The emission dopant of this invention will now be described.

As an emission dopant used in this invention, a fluorescent compound (also referred to as a fluorescent compound) or a phosphorescence dopant (also referred to as a phosphorescence emission material, a phosphorescence compound, or a phosphorescence emitting compound) are employed. The emission dopant (also referred to simply as a emission material) employed in the emission layer or emission unit of the organic EL element according to this invention preferably contains the host compound described above as well as a phosphorescence dopant.

Phosphorescence Emission Dopant

A phosphorescence emission dopant according to this invention will be described.

The phosphorescence emitting material is a compound which emits light from the excited triplet, which is specifically a compound which emits phosphorescence at room temperature (25° C.), and is defined to exhibit a phosphorescent quantum yield at 25° C. of not less than 0.01, and the phosphorescent quantum yield at 25° C. is preferably not less than 0.1.

The phosphorescent quantum yield can be measured according to a method described in the fourth edition "Jikken Kagaku Koza 7", Bunko II, page 398 (1992) published by Maruzen. The phosphorescent quantum yield in a solution can be measured employing various kinds of solvents. The phosphorescence emitting material of the present invention is a compound, in which the phosphorescent quantum yield measured employing any one of the solvents falls within the above-described range (0.01 or more).

The light emission of the phosphorescence emitting material is divided in two types in principle, one is an energy transfer type in which recombination of a carrier occurs on the host to which the carrier is transported to excite the host, the resulting energy is transferred to the phosphorescent compound, and light is emitted from the phosphorescent compound, and the other is a carrier trap type in which recombination of a carrier occurs on the phosphorescent compound which is a carrier trap material, and light is emitted from the phosphorescent compound. However, in each type, energy level of the phosphorescent compound in excited state is lower than that of the host in excited state.

The phosphorescence emitting material can be optionally selected from the known phosphorescence emitting materials used in the light emission layer of an organic EL element.

The phosphorescence emitting material is preferably a complex containing a metal of Group 8-10 of the periodic table, and more preferably an iridium compound, an osmium compound, a platinum compound (a platinum complex compound) or a rare-earth metal complex. Of these, most preferable is an iridium compound.

Specific examples of a compound used as a phosphorescence emitting material are shown below, however, the present invention is not limited thereto. These compounds can be synthesized, for example, according to a method described in Inorg. Chem., 40, 1704-1711.

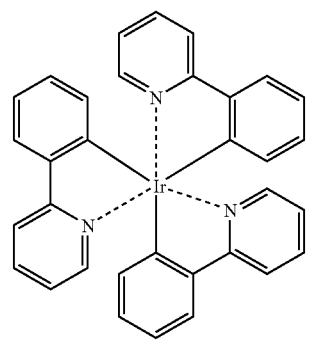

Ir-1

Ir-2
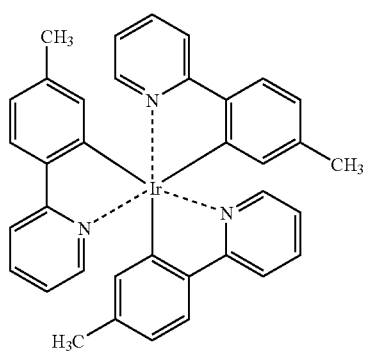
Ir-3
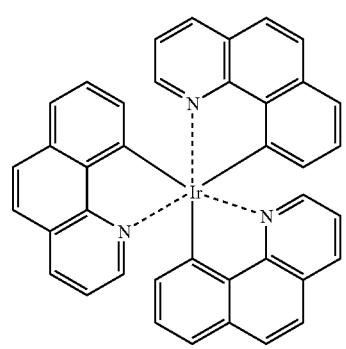
Ir-4
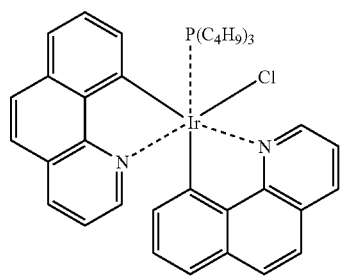
Ir-5
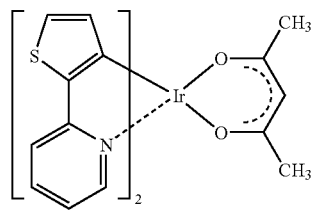
Ir-6
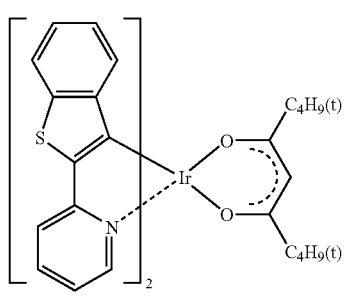
Ir-7
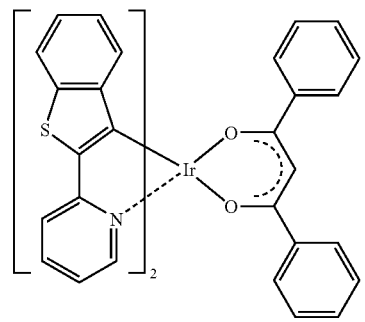
Ir-8
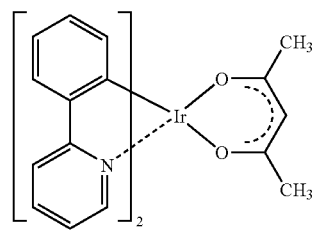
Ir-9
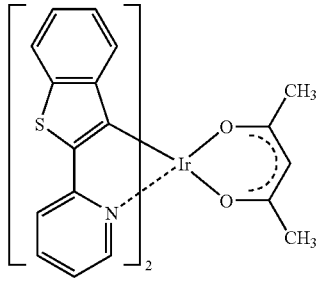
Ir-10
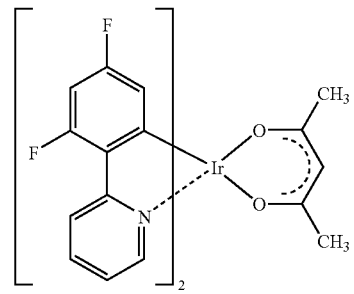
Ir-11
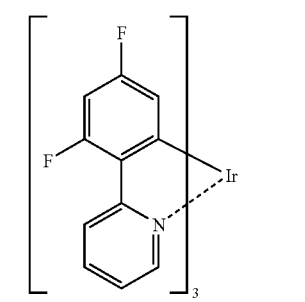

Ir-12
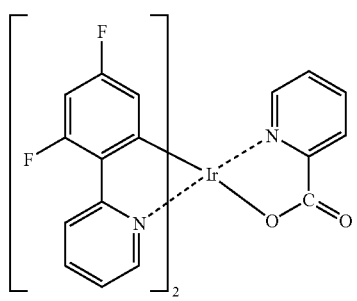
Ir-13
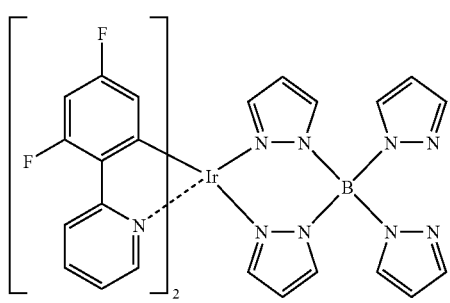
Ir-14
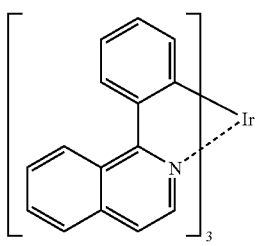
Pt-1
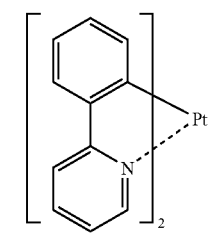
Pt-2
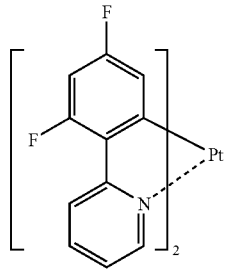
Pt-3
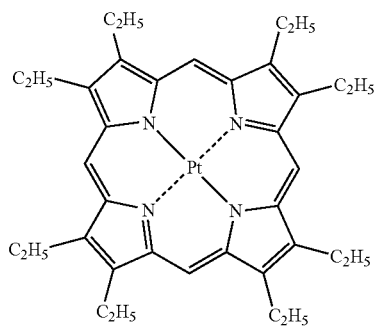
A-1
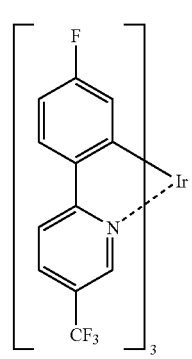
D-1
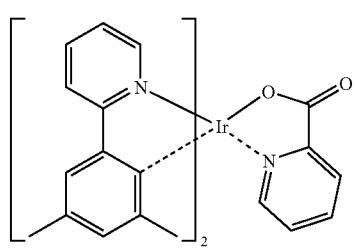
D-2
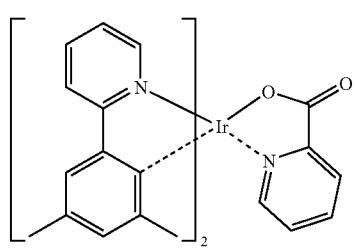
D-3

-continued

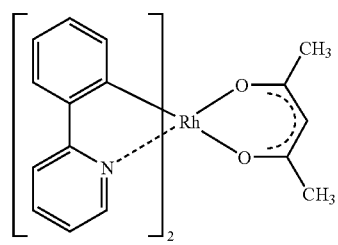  D-4

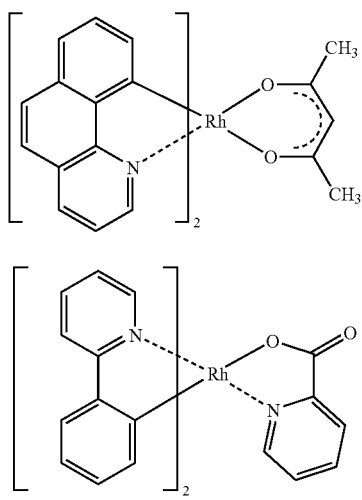  D-5

D-6

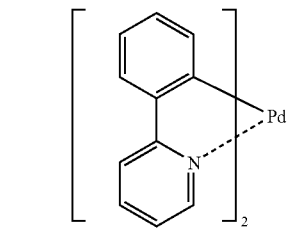  Pd-1

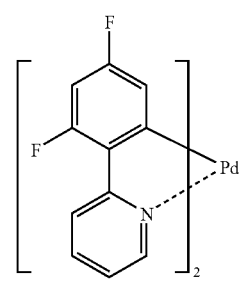  Pd-2

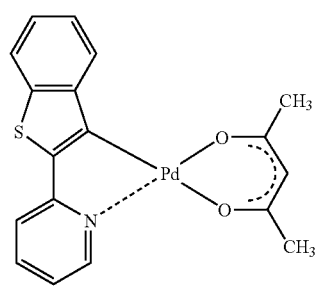  Pd-3

-continued

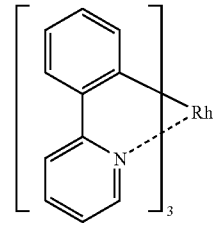  Rh-1

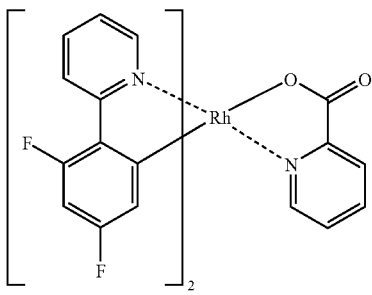  Rh-2

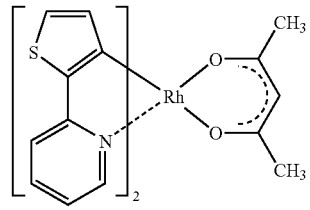  Rh-3

<Fluorescent Emission Dopant (Fluorescent Emission Compound)>

A typical example of the fluorescent emission dopant (a fluorescent dopant) includes coumarin type dye, pyran type dye, cyanine type dye, croconium type dye, squalium type dye, oxobenzanthracene type dye, fluorescein type dye, rhodamine type dye, pyrilium type dye, perylene type dye, stilbene type dye, polythiophene type dye or rare earth complex type fluorescent substances.

An injection layer, an inhibition layer, an electron transport layer etc., are described.

<<Injection Layer: Electron Injection Layer, Positive Hole Injection Layer>>

An injection layer is provided when it is necessary and includes an electron injection layer and a positive hole injection layer, which may be arranged between an anode and an emission layer or a positive transfer layer, and between a cathode and an emission layer or an electron transfer layer, as described above.

An injection layer is a layer which is arranged between an electrode and an organic layer to decrease an driving voltage and to improve an emission luminance, which is detailed in volume 2, chapter 2 (pp. 123-166) of "Organic EL Elements and Industrialization Front thereof (Nov. 30, 1998, published by N. T. S. Inc.)", and includes a positive hole injection layer (an anode buffer layer) and an electron injection layer (a cathode buffer layer).

An anode buffer layer (a positive hole injection layer) is also detailed in such as JP-A H09-45479, JP-A H09-260062 and JP-A H08-288069, and specific examples include such as a phthalocyanine buffer layer represented by such as copper phthalocyanine, an oxide buffer layer represented by such as vanadium oxide, an amorphous carbon buffer layer, and a polymer buffer layer employing conductive polymer such as polyaniline (emeraldine) and polythiophene.

A cathode buffer layer (an electron injection layer) is also detailed in such as JP-A H06-325871, JP-A H09-17574 and JP-A H10-74586, and specific examples include a metal buffer layer represented by strontium, aluminum and so on, an alkali metal compound buffer layer represented by lithium fluoride, an alkali metal earth compound buffer layer represented by magnesium fluoride and an oxide buffer layer represented by aluminum oxide. The above-described buffer layer (injection layer) is preferably a very thin layer, and the layer thickness is preferably in a range of 0.1 nm-5 µm although it depends on a raw material.

<Inhibition Layer: Positive Hole Inhibition Layer, Electron Inhibition Layer>

An inhibition layer is provided in addition to an elemental layer arrangement of the organic compound layer as described above. There is, for example, a positive inhibition (hole block) layer described in such as JP-A H11-204258 and JP-A H11-204359 and p. 273 of "Organic EL Elements and Industrialization Front Thereof (Nov. 30 (1998), published by NTS. Inc)".

A positive hole inhibition layer, in a broad meaning, is provided with a function of electron transport layer, being comprised of a material having a function of transporting an electron but a very small ability of transporting a positive hole, and can improve the recombination probability of an electron and a positive hole by inhibiting a positive hole while transporting an electron. Further, an arrangement of an electron transport layer described later can be appropriately utilized as a positive hole inhibition layer according to this invention.

The positive hole inhibition layer of the organic EL element of this invention is preferably provided adjacent to an emission layer.

It is preferred that a positive hole inhibition layer contains an azacarbazole derivative recited as an example of a host compound.

When the element comprises a plural number of emission layers of different emission colors, an emission layer, an emission maximum wavelength of which is shortest, is preferably arranged nearest to an anode among the all emission layers, however, in such a case, a hole block layer is preferably additionally arranged between said shortest wavelength layer and an emission layer second nearest to an anode. Further, not less than 50 weight % of a compound contained in a hole block layer arranged at said position has a larger ionization potential by not less than 0.3 eV against a host compound of the aforesaid shortest wavelength layer.

An ionization potential is defined by an energy required to release an electron existing on the HOMO (highest occupied molecular orbit) level to a vacuum level, and for example, can be determined according to the following method.

(1) By use of Gaussian 98 (Gaussian 98, Revision A. 11. 4, M. J. Frisch, et al, Gaussian, Inc., Pittsburgh Pa., 2002), which is a molecular orbit calculation software manufactured by Gaussian, Inc., USA; a value calculated by performing structural optimization (converted value of eV unit), the second place of decimals of which is rounded off, is defined as an ionization potential.

(2) An ionization potential can be also determined by being directly measured by means of photoelectron spectroscopy. Foe example, a low energy electron spectrometer "Model AC-1" manufactured by Riken Keiki Co., Ltd., or a method known as ultraviolet photoelectron spectroscopy can be preferably utilized.

On the other hand, an electron inhibition layer is, in a broad meaning, provided with a function of a positive hole transport layer, being comprised of a material having a function of transporting a positive hole but a very small ability of transporting an electron, and can improve the recombination probability of an electron and a positive hole by inhibiting an electron while transporting a positive hole. Further, an arrangement of a positive hole transport layer described later can be appropriately utilized as an electron inhibition layer. Thickness of the positive hole inhibition layer and electron transport layer is preferably 3-100 nm, and more preferably 5-30 nm.

<Positive Hole Transport Layer>

A positive hole transport layer contains a material having a function of transporting a positive hole, and in a broad meaning, a positive hole injection layer and an electron inhibition layer are also included in a positive hole transport layer. A single layer of or plural layers of a positive hole transport layer may be provided.

A positive hole transport material is those having any one of a property to inject or transport a positive hole or a barrier property to an electron, and may be either an organic material or an inorganic material. For example, listed are a triazole derivative, an oxadiazole derivative, an imidazole derivative, a polyarylalkane derivative, a pyrazoline derivative, a pyrazolone derivative, a phenylenediamine derivative, an arylamine derivative, an amino substituted chalcone derivative, an oxazole derivatives, a styrylanthracene derivative, fluorenone derivative, a hydrazone derivative, a stilbene derivative, a silazane derivative, an aniline type copolymer, or conductive high molecular oligomer, specifically preferably such as thiophene oligomer.

As a positive hole transport material, those described above can be utilized, however, it is preferable to utilize a porphyrin compound, an aromatic tertiary amine compound and a styrylamine compound, and specifically preferably an aromatic tertiary amine compound.

Typical examples of an aromatic tertiary amine compound and a styrylamine compound include N,N,N',N'-tetraphenyl-4,4'-diaminophenyl; N,N'-diphenyl-N,N'-bis(3-methylphenyl)-(1,1'-biphenyl)-4,4'-diamine (TDP); 2,2-bis(4-di-p-tolylaminophenyl)propane; 1,1-bis(4-di-p-tolylaminophenyl)cyclohexane; N,N,N',N'-tetra-p-tolyl-4,4'-diaminobiphenyl; 1,1-bis(4-di-p-tolylaminophenyl)-4-phenylcyclohexane; bis(4-dimethylamino-2-methylphenyl) phenylmethane; bis(4-di-p-tolylaminophenyl) phenylmethane; N,N'-diphenyl-N,N'-di(4-methoxyphenyl)-4,4'-diaminobiphenyl; N,N,N',N'-tetraphenyl-4,4'-diaminodiphenyl ether; 4,4'-bis(diphenylamino) quadriphenyl; N,N,N-tri(p-tolyl)amine; 4-(di-p-tolylamino)-4'-[4-(di-p-tolylamino)styryl]stilbene; 4-N,N-diphenylamino-(2-diphenylvinyl)benzene; 3-methoxy-4'-N,N-diphenylaminostilbenzen; and N-phenylcarbazole, in addition thereto, those having two condensed aromatic rings in a molecule described in U.S. Pat. No. 5,061,569, such as 4,4'-bis[N-(1-naphthyl)-N-phenylamino]biphenyl (NDP), and 4,4',4''-tris[N-(3-methylphenyl)-N-phenylamino]triphenylamine (MTDATA), in which three of triphenylamine units are bonded in a star burst form, described in JP-A H04-308688.

A polymer in which the material mentioned above is introduced in the polymer chain or a polymer having the material as the polymer main chain can be also used. As the hole injecting material or the hole transporting material, inorganic compounds such as p-type Si and p-type SiC are usable.

A so-called p-type hole blocking layer as disclosed in JP-A H 11-251067 or described in the literature of J. Huang et al.

(Applied Physics Letters 80 (2002), p. 139) is also applicable. In the present invention, these materials are preferably utilized since an emitting element exhibiting a higher efficiency is obtained.

This positive hole transport layer can be provided by forming a thin layer made of the above-described positive hole transport material according to a method known in the art such as a vacuum evaporation method, a spin coating method, a cast method, an inkjet method and a LB method. The layer thickness of a positive hole transport layer is not specifically limited, however, is generally 5 nm-5 µm, and preferably 5-200 nm. This positive transport layer may have a single layer structure comprised of one or two or more types of the above described materials.

A positive hole transport layer having high p-type property doped with impurity can be utilized. Example thereof includes those described in JP-A-H04-297076, JP-A-2000-196140, JP-A-2001-102175, and J. Appl. Phys., 95, 5773 (2004) and so on.

It is preferable to employ such a positive hole transport layer having high p-type property, since an element with lower power consumption can be prepared in this invention.

<Electron Transport Layer>

An electron transport layer is composed of a material having a function of transporting an electron, and in a broad meaning, an electron transport layer and a positive hole inhibition layer are also included in a positive hole transport layer. A single layer of or plural layers of an electron transport layer may be provided.

The electron transfer material (it works as a positive hole inhibition layer, simultaneously), which is employed in a single electron transfer layer and an electron transfer layer provided adjacent to cathode side with respect to emission layer when it is used as plural layers, is sufficient to have a function to transmit an electron injected from a cathode to an emission layer, and compounds conventionally known in the art can be utilized by arbitrarily selection as a material thereof. Any one can be employed by selecting from conventionally known compounds as its material. Examples of a material include such as a nitro-substituted fluorene derivative, a diphenylquinone derivative, a thiopyrandioxide derivative, carbodiimide, a fleorenylidenemethane derivative, anthraquinonedimethane and anthrone derivatives. Further, a thiazole derivative in which an oxygen atom in the oxadiazole ring of the above-described oxadiazole derivative is substituted by a sulfur atom, and a quinoxaline derivative having a quinoxaline ring which is known as an electron attracting group can be utilized as an electron transfer material. Polymer materials, in which these materials are introduced in a polymer chain or these materials form the main chain of polymer, can be also utilized.

Further, a metal complex of a 8-quinolinol derivative such as tris(8-quinolinol) aluminum (Alq), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum and bis(8-quinolinol)zinc (Znq); and metal complexes in which a central metal of the aforesaid metal complexes is substituted by In, Mg, Cu, Ca, Sn, Ga or Pb, can be also utilized as an electron transfer material. Further, metal-free or metal phthalocyanine, or those the terminal of which is substituted by an alkyl group and a sulfonic acid group, can be preferably utilized as an electron transfer material. Further, distyrylpyrazine derivative, which has been exemplified as a material of an emission layer, can be also utilized as an electron transfer material, and, similarly to the case of a positive hole injection layer and a positive hole transfer layer, an inorganic semiconductor such as an n-type-Si and an n-type-SiC can be also utilized as an electron transfer material The electron transport layer can be provided by forming a thin layer made of the above-described electron transport material according to a method known in the art such as a vacuum evaporation method, a spin coating method, a cast method, an inkjet method and a LB method. The layer thickness of an electron transport layer is not specifically limited; however, is generally 5 nm-5 µm, preferably 5-200 nm. This electron transport layer may have a single layer structure comprised of one or not less than two types of the above described materials.

An electron transport layer having high n-type property doped with impurity can be utilized. Example thereof includes those described in JP-A-H04-297076, JP-A-H10-270172, JP-A-2000-196140, JP-A-2001-102175, and J. Appl. Phys., 95, 5773 (2004) and so on.

It is preferable to employ such an electron transport layer having high n-type property, since an element with lower power consumption can be prepared in this invention.

<Anode>

As an anode according to an organic EL element of this invention, those comprising metal, alloy, a conductive compound, which has a large work function (not less than 4 eV), and a mixture thereof as an electrode substance are preferably utilized. Specific examples of such an electrode substance include a conductive transparent material such as metal like Au, CuI Indium tin oxide (ITO), $SnO_2$ and ZnO. Further, a material such as IDIXO ($In_2O_3$—ZnO), which can prepare an amorphous and transparent electrode, may be also utilized. As for an anode, these electrode substances may be made into a thin layer by a method such as evaporation or spattering and a pattern of a desired form may be formed by means of photolithography, or in the case of requirement of pattern precision is not so severe (not less than 100 µm), a pattern may be formed through a mask of a desired form at the time of evaporation or spattering of the above-described substances. When emission is taken out of this anode, the transmittance is preferably set to not less than 10% and the sheet resistance as an anode is preferably not more than a several hundreds $\Omega/\square$. Further, although the layer thickness depends on a material, it is generally selected in a range of 10-1,000 nm and preferably of 10-200 nm.

<Cathode>

On the other hand, as a cathode according to this invention, metal, alloy, a conductive compound and a mixture thereof, which have a small work function (not more than 4 eV), are utilized as an electrode substance. Specific examples of such an electrode substance includes such as sodium, sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture and rare earth metal.

Among them, with respect to an electron injection property and durability against such as oxidation, preferable are a mixture of electron injecting metal with the second metal which is stable metal having a work function larger than electron injecting metal, such as a magnesium/silver mixture, a magnesium/aluminum mixture, a magnesium/indium mixture, an aluminum/aluminum oxide ($Al_2O_3$) mixture and a lithium/aluminum mixture, and aluminum. A cathode can be provided by a method such as evaporation or spattering to form a thin layer. Further, the sheet resistance as a cathode is preferably not more than a several hundreds $\Omega/\square$ and the layer thickness is generally selected in a range of 10 nm-5 µm and preferably of 50-200 nm. Herein, to transmit emission, either one of an anode or a cathode of an organic EL element is preferably transparent or translucent to improve the mission luminance.

A transparent or translucent cathode may be prepared by a method in which the above mentioned metal is provided on the anode with a thickness of 1-20 nm and then electroconductive transparent material described as the anode. An element having both transparent anode and cathode may be prepared by applying this method.

<Substrate>

A substrate (also referred to as Base Body, Base Plate, Base Material or Support) according to an organic EL element of this invention is not specifically limited with respect to types of such as glass and plastics being transparent or opaque, however, a substrate preferably utilized includes such as glass, quartz and transparent resin film. A specifically preferable substrate is resin film capable of providing an organic EL element with a flexible property.

Resin film includes polyester such as polyethylene terephthalate (PET) and polyethylene naphthalate (PEN), polyethylene, polypropylene, cellophane, cellulose ester and its derivatives such as cellulose diacetate, cellulose triacetate, cellulose acetate butylate, cellulose acetate propionate (CAP), cellulose acetate phthalate (TAC), and cellulose nitrate, polyvinylidene chloride, polyvinylalcohol, polyethylenevinylalcohol, syndiotactic polystyrene, polycarbonate, norbornane resin, polymethylpentene, polyetherketone, polyimide, polyether sulfone (PES), polyphenylene sulfide, polysulfones, polyether imide, polyetherketone imide, polyamide, fluorine resin, nylon, polymethyl methacrylate, acryl or acrylates, cyclo-olefin resin such as ARTON (commercial name, manufactured by JSR Corp.) or APEL (commercial name, manufactured by Mitsui Chemicals Inc.).

On the surface of resin film, an inorganic or organic cover layer or a hybrid cover layer comprising the both may be formed, and the film is preferably provided with a high barrier ability having a vapor permeability of not more than 0.01 g/m$^2$·24 hr (at 25±0.5° C., 90±2% RH) measured by a method stipulated by JIS K 7129-1992, and more preferably a high barrier ability having an oxygen permeability of not more than 10 ml/(m$^2$·24 hr·MPa) as well as a vapor permeability of not more than $10^{-3}$ g/m$^2$·24 hr, measured by a method stipulated by JIS K 7126-1987.

Any materials capable of preventing penetration of substance causing degradation of the element such as moisture and oxygen are usable for forming the barrier layer. For example, silicon oxide, silicon dioxide and silicon nitride are usable. It is more preferable to give a laminated layer structure composed of such the inorganic layer and a layer of an organic material to the barrier layer for improving the fragility of the layer. It is preferable that the both kinds of layers are alternatively piled for several times though there is no limitation as to the laminating order of the inorganic layer and the organic layer.

<<Barrier Layer Forming Method>>

The method for forming the barrier layer is not specifically limited and, for example, a vacuum deposition method, spattering method, reaction spattering method, molecule beam epitaxy method, cluster-ion beam method, ion plating method, plasma polymerization method, atmosphere pressure plasma polymerization method, plasma CVD method, laser CVD method, heat CVD method and coating method are applicable, and the atmosphere pressure plasma polymerization method such as that described in JP A 2004-68143 is particularly preferable.

As the opaque substrate, for example, a plate of metal such as aluminum and stainless steel, a film or plate of opaque resin and a ceramic substrate are cited.

Take out efficiency of an organic EL element of the present invention at room temperature is preferably not less than 1%, and more preferably not less than 5%. Herein, take out quantum efficiency (%)=a number of photons emitted outside of an organic EL element/a number of electrons flown in an organic EL element×100.

Further, a hue improving filter such as a color filter may be utilized together, and a color conversion filter, which converts emission color from an organic EL element into multicolor by use of a fluorescent substance, may be also utilized together. In the case of utilizing a color conversion filter, λmax of emission of an organic EL element is preferably not more than 480 nm.

<<Sealing>>

As the sealing means, a method for pasting together with a sealing material, the electrodes and the substrate by an adhesive agent is applicable.

The sealing material is placed so as to cover the displaying area of the organic EL element and may have a flat plate shape or a concave plate shape, and the transparence and the electric insulation property of it are not specifically limited.

Concretely, a glass plate, polymer plate, polymer film, metal plate and metal film can be cited. As the glass plate, a plate of soda-lime glass, barium strontium-containing glass, lead glass, alumino silicate glass, boron silicate glass and quartz are usable. As the polymer plate, a plate of polycarbonate, acryl resin, polyethylene terephthalate), polyether sulfide and polysulfone are usable. As the metal plate, a plate composed of one or more kinds of metal selected from stainless steel, iron, copper, aluminum, magnesium, nickel, zinc, chromium, titanium, molybdenum, silicon, germanium and tantalum and an alloy of them are cited.

In this invention, the polymer film and the metal film are preferably used by which the element can be made thinner. The polymer film having an oxygen permeability of not more than $1 \times 10^{-3}$ ml/(m$^2$·24 hr·MPa), measured by a method stipulated by JIS K 7126-1987, and a vapor permeability of not more than $1 \times 10^{-5}$ g/m$^2$·24 hr (at 25±0.5° C., 90±2% RH) measured by a method stipulated by JIS K 7129-1992.

A sandblast treatment and a chemical etching treatment are applicable for making the sealing material into the concave shape.

A photo-curable and thermo-curable adhesive agents containing a reactive vinyl group of acryl type oligomer and a methacryl type oligomer, and a moisture curable adhesive agent such as 2-cyanoacrylate can be cited as the adhesive agent. Epoxy type thermally and chemically (two liquid type) curable adhesive agents are applicable Hot-melt type polyamide, polyester and polyolefin adhesive agents are applicable. Cationic curable type UV curable epoxy adhesive agent is also usable.

The organic EL element is degraded by heat in some cases, therefore, the adhesive agent capable of being cured to adhere within the temperature range of from room temperature to 80° is preferred A moisture absorbing agent may be dispersed in the adhesive agent. Coating of the adhesive agent onto the adhering portion may be performed by a dispenser available on the market or printing by a screen printing.

It is preferable that an inorganic or organic layer is provided on outside of the electrode placed on the side of facing to the substrate through an organic layer so as to cover the electrode and the organic layer and contact with the substrate to form a sealing layer. In such the case, the material for forming the sealing layer may be a material having a function to inhibit permeation of a substance causing degradation such as water and oxygen, and silicon oxide, silicon dioxide and silicon nitride are usable for example. The layer preferably has a laminated structure composed of an inorganic material and an organic material. As the method for forming such the layer, a vacuum deposition method, spattering method, reaction spattering method, molecule beam epitaxy method, cluster-ion beam method, ion plating method, plasma polymerization method, atmosphere pressure plasma polymerization method, plasma CVD method, laser CVD method, heat CVD method and coating method are applicable.

In the space between the sealing material and the displaying portion of the organic EL element, an inactive gas such as nitrogen and argon or an inactive liquid such as silicone oil is preferably injected. The space may be made vacuum. A moisture absorbing compound may be enclosed in the element.

Examples of the moisture absorbing compound include a metal oxide such as sodium oxide, potassium oxide, calcium oxide, barium oxide, magnesium oxide and aluminum oxide, a sulfate such as sodium sulfate, calcium sulfate, magnesium sulfate and cobalt sulfate, a metal halide such as calcium chloride, magnesium chloride, cesium fluoride, tantalum fluoride, cerium bromide, magnesium bromide, barium iodide and magnesium iodide, and a perchlorate such as barium perchlorate and magnesium perchlorate. Anhydrate is preferable as to the sulfate, halide and perchlorate.

<<Protection Layer and Protection Plate>>

For raising the mechanical strength of the element, a protection layer or a protection plate may be provided on outside of the sealing layer of the side facing to the substrate through the organic layer or the outside of the sealing film. Such the protection layer or plate is preferably provided since the strength of the element is not always so high when the sealing is carried out by the foregoing sealing layer. The glass plate, polymer plate, polymer film and plate, and metal film and plate the same as those to be used for sealing are usable for such the protection material. Polymer film is preferably used from the viewpoint of light weight and less thickness.

Taking Out Light

Generally it is said that, in the organic EL element of this invention, light is emitted in a layer of which refractive index is higher (the refractive index is about 1.7 to 2.1) than that of air, and only 15 to 20% of the light emitted in the light emission layer can be taken out. This is because the light which enters into the interface (interface of a transparent substrate and air) with the angle larger than a critical angle cannot be taken out of the element due to the total internal reflection, or because the light is totally reflected between the transparent substrate and the transparent electrode or between the transparent substrate and the light emission layers resulting in being wave-guided in the transparent electrode or in the light emission layer to get away to the side of the element.

Examples of a method to improve the efficiency of taking out of the light include: a method to form concavity and convexity on the surface of the transparent substrate to prevent total internal reflection at the interface between the transparent substrate and air (for example, refer to U.S. Pat. No. 4,774,435); a method to provide a light converging function to the substrate (for example, refer to JP-A S63-314795); a method to provide a reflecting surface on the side of the element (for example, refer to JP-A No. 01-220394); a method to provide a flat layer between the substrate and the light emission layer, the flat layer having an intermediate refractive index to form an anti-reflection layer (for example, refer to JP-A S62-172691); a method to provide a flat layer having a low refractive index between the substrate and the light emission layer (for example, JP-A 2001-202827); and a method to provide a diffraction grating between any of the substrate, transparent electrode and light emission layer (including the interlayer between the substrate and out side air) (for example refer to JP-A H11-283751).

These methods can be used in combination with the organic electroluminescence element of the present invention. Also, a method of forming a flat layer having a lower refractive index than that of the substrate between the substrate and the light emission layer, or a method of forming a diffraction grating between any of the substrate, transparent electrode and light emission layer (including the interlayer between the substrate and out side air) can be preferably used.

An element exhibiting further higher luminance and durability can be obtained by combining these methods, in the present invention.

The light-extracting efficiency of light which comes out of the transparent electrode increases with decreasing refractive index when a low refractive index medium having a thickness larger than the wavelength of the light is formed between the transparent electrode and the transparent substrate.

As a low refractive index layer, aerogel, porous silica, magnesium fluoride and fluorine-containing polymer, are cited, for example. Since the refractive index of the transparent substrate is generally 1.5 to 1.7, the refractive index of the low refractive index layer is preferably 1.5 or less and more preferably 1.35 or less.

The thickness of a low refractive index medium is preferably more than twice of the wavelength of the light in the medium, because when the thickness of the low refractive index medium, where the electromagnetic wave exuded as an evanescent wave enters into the transparent substrate, and the effect of the low refractive index layer is reduced.

The method to provide a diffraction grating at the interface where the total internal reflection occurs or in some of the medium has a feature that the effect of enhancing the light-extracting efficiency is high. The intension of this method is to take out the light which cannot come out due to such as total internal reflection between the layers among the light emitted in the light emission layer, by providing a diffraction grating between any of the layers or in any of the mediums (in the transparent substrate or in the transparent electrode), using the property of the diffraction grating that it can change the direction of light to a specified direction different from the direction of reflection due to so-called Bragg diffraction such as primary diffraction or secondary diffraction.

The diffraction grating to be provided preferably has a two-dimensional periodic refractive index. This is because, since the light is emitted randomly to any direction, only the light proceeds to a specific direction can be diffracted when a generally used one-dimensional diffraction grating having a periodic refractive index only in a specific direction is used, whereby the light-extracting efficiency is not largely increases. However, by using diffraction grating having a two-dimensionally periodic refractive index, the light proceeds any direction can be diffracted, whereby the light-extracting efficiency is increased.

The diffraction grating may be provided between any of the layers on in any of the mediums (in the transparent substrate or in the transparent electrode), however, it is preferably provided in the vicinity of the organic light emission layer where the light is emitted.

The period of the diffraction grating is preferably ½ to 3 times of the wavelength of the light in the medium.

The array of the diffraction grating is preferably two-dimensionally repeated, for example, as in the shape of a square lattice, a triangular lattice, or a honeycomb lattice.

<<Light-Condensing Sheet>>

In the organic electroluminescence element of the present invention, the luminance in the specified direction, for example, the front direction against the emitting plane of the element can be increased, for example, by processing to form a structure of a micro-lens array or in combination with a so-called light-condensing sheet on the light-extracting side surface of the substrate.

As an example of a micro-lens array, quadrangular pyramids 30 μm on a side and having a vertex angle of 90° are two-dimensionally arranged on the light extracting side surface of the substrate. The side of the quadrangular pyramids is preferably 10-100 μm. When the length of the side is shorter than the above range, the light is colored due to the effect of diffraction, and when it is longer than the above range, it becomes unfavorably thick.

As a light-condensing sheet, the one practically applied for an LED backlight of a liquid crystal display is applicable. Examples of such a sheet include a brightness enhancing film (BEF) produced by SUMITOMO 3M Inc. As the shape of the prism, triangle-shaped strip having a vertex angle of 90° and a pitch of 50 μm, the one having round apexes, or the one having a randomly changed pitch may be included.

In order to control the luminous radiation angle of the light emitting element, a light diffusion plate and a film may be used in combination with the light-condensing sheet. For example, a diffusion film (light-up) produced by KIMOTO Co., Ltd. can be used.

<Preparation Method of Organic EL Element>

As an example or a preparation method of an organic EL element of this invention, a preparation method of an organic EL element, comprising anode/positive hole injection layer/positive hole transport layer/emission layer/positive hole inhibition layer/electron transport layer/cathode, will be described.

First, on an appropriate substrate, a thin layer comprising a desired electrode substance such as an anode electrode substance is formed by means of evaporation or spattering so as to make a layer thickness of not more than 1 μm and preferably of 10-200 nm, whereby an anode is prepared.

Next, thin layers containing organic substances of such as a positive hole injection layer, a positive hole transport layer, an emission layer, a positive hole inhibition layer and an electron transport layer are formed on this layer.

A thin layer forming method of these layers containing organic substances includes such as an evaporation method and a wet process (a spin coat method, a cast method, an inkjet method, and a printing method) as described before, and, a vacuum evaporation method, a spin coat method, inkjet method, or a printing method is specifically preferable with respect to easy preparation of a homogeneous layer and bare generation of pinholes.

The following organic solvent may be employed for a liquid medium to dissolve or disperse an organic EL element material according to this invention; a ketone compound such as methylethyl ketone, and cyclohexanone; an aliphatic acid ester compound such as ethylacetate; a halogenated hydrocarbon compound such as dichlorobenzene; an aromatic hydrocarbon compound such as toluene, xylene, mesitylene, and cyclohexyl benzene; an aliphatic hydrocarbon compound such as cyclohexane, decalin, and dodecane; DMF and DMSO. A dispersion method such as ultrasonic dispersion, high shearing force dispersion and media dispersion may be applicable.

After formation of these layers, a thin layer comprising a cathode electrode substance is formed thereon by means of such as evaporation or spattering so as to make a layer thickness of 1 μm or less, preferably in a range of 50-200 nm to provide a cathode, whereby a desired organic EL element can be prepared.

Further, reversing the preparation order, it is also possible to prepare layers in the order of a cathode, an electron transport layer, a positive hole inhibition layer, an emission layer, a positive hole transport layer and an anode. When a direct current voltage is applied on the multicolor display device thus prepared, emission can be observed by application of a voltage of approximately 2-40 V setting an anode to + (plus) polarity and a cathode to − (minus) polarity. Further, no current flows and no emission generate at all even when a voltage is applied with a reversed polarity. Further, in the case of alternate current voltage being applied, emission generates only in a state of an anode being + and a cathode being −. Herein, the wave shape of alternate current may be arbitrary.

<<Use>>

The organic EL element of the invention can be used as a displaying device, display, and various kinds of light source. As the light source, domestic illumination, car interior illumination, backlight of watches or liquid crystal displays, sign boards, signals, light source of photo memories, light source of electrophotographic copying machine, light source of light communication processor and light source of light sensors though the use is not limited to the above. Particularly, the device is suitably used in combination with a color filter as the backlight of the liquid crystal display or the light source of illumination.

A patterning may be provided via metal mask or inkjet printing method during production to the organic EL element of this invention if necessary. Patterning is conducted to only an electric pole, an electric pole and an emission layer or the elements a whole in this instance, and known method can be employed.

Figure 4:
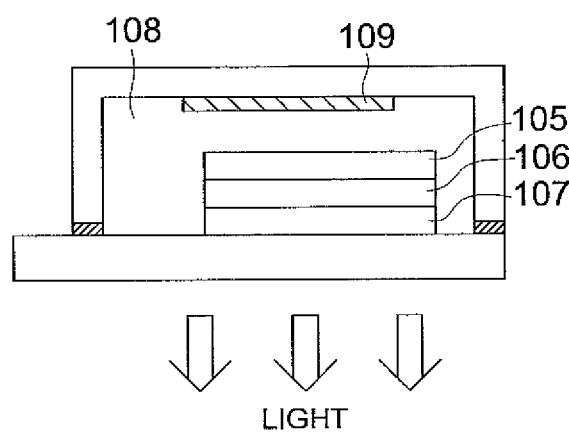
FIG. 4 is a cross-sectional view of an illuminating device.
1 display
3 pixels
5 scanning line
6 data line
A display section
B controlling section
107 glass substrate fitted with transparent electrodes
106 organic EL layer
105 cathode
102 glass cover
108 nitrogen gas
109 desiccating agent

Color of emission from an organic EL element of the present invention and from a compound according to the present invention is determined by a color when a measured result by use of Spectral Radiation Luminance Meter CS-100 (manufactured by Konica Minolta Sensing Corp.) according to p. 108, FIG. 4.16 in "New Edition Color Science Handbook" (Edited by Japan Color Society, University of Tokyo Press, 1985) is applied into CIE chromaticity coordinates.

A white element in the present invention refers that chromaticity in CIE 1931 color specification system at 1,000 $Cd/m^2$, when a front luminance at 2° viewing angle is measured by the above-described method, is within a region of $X=0.33\pm0.07$, $Y=0.33\pm0.1$.

EXAMPLES

The present invention will now be described with reference to examples, however the present invention is not limited thereto.

Further, shown are structures of the compounds employed in the following examples.

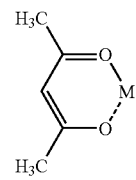

L-231

-continued

L-232
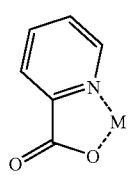

L-233
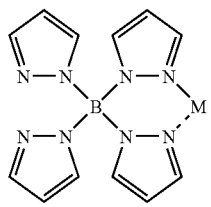

L-234
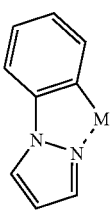

BD-546 (Comparative Compound)
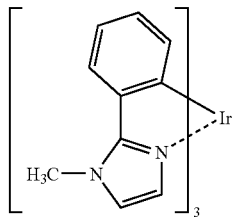

BD-547
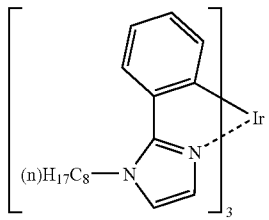

m-CP
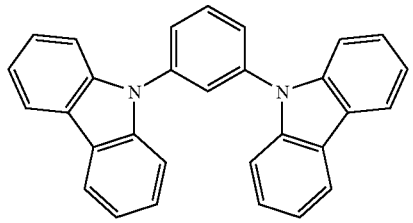

Example 1

Synthesis of Exemplified Compound BD-6

Ligand L-3 was synthesized as described below, and by employing above Ligand L-3, Exemplified Compound BD-6 of the present invention was synthesized.

<<Synthesis of Ligand L-3>>

Dissolved in 40 ml of tetrahydrofuran (THF) were 4(n-octyl)phenylboronic acid (15.2 g, 65 mmol) and 1,3-dibromobenzene (11.8 g, 50 mmol), and 10 ml of pure water and potassium carbonate (17.3 g, 125 mmol), followed by replacement of the interior system with nitrogen.

After complete replacement with nitrogen, tetrakistriphenylphosphine palladium (PD(O)) (2.9 g, 2.5 mmol) was added, and heated reflux was carried out over 8 hours. After completing the reaction, conventional extraction, drying, and purification via column chromatography were carried out, whereby Compound 1 was prepared at a yield of 65% (11.2 g). According to a conventional method, boronic acid 2 was regulated. Thereafter, by employing above boronic acid 2 (10.2 g, 33 mmol) and 2-bromo-N-methylimidazole (4.8 g, 30 mmol), targeted Ligand L-3 was prepared at a yield of 78% (8.1 g) under Suzuki coupling conditions which were the same as above. Formation of each intermediate and Ligand L-3 was confirmed via mass spectra, $^1$H-NMR.

<<Synthesis of Exemplified Compound BD-6>>

Under nitrogen flow, above Ligand L-3 (0.35 g, 1.0 mmol) and iridium trichloride trihydrate (0.12 mg, 0.25 mmol) were heat-refluxed for 12 hours in a mixed solvent of 10 ml of ethoxyethanol and 1 ml of pure water. After completion of the reaction, re-precipitation was carried out in methanol, whereby 0.20 g of a yellow solid was prepared. Each of the resulting yellow solids (0.20 g), Ligand L-3 (0.18 g, 0.5 mmol), and silver trifluoromethane sulfonate (0.68 g, 0.3 mmol) was weighed and all were placed in a sealable test tube. After three deaeration-nitrogen replacements, the test tube was sealed and heated in an oil bath at 130° C. for 4 days. After completion of the reaction, purification was carried out via column chromatography, whereby 35 mg (at a yield of 11% employing iridium chloride as a standard) of targeted BD-6 was prepared. Formation was confirmed via $^1$H-NMR.

Further, in the same manner as above, it is possible to synthesize the other compounds (also referred to as metal complexes) of the present invention by referring to the methods described in references such as Organic Letter, Vol 3, No. 16, pages 2,579-2,581 (2001); Inorganic Chemistry, Volume 30, No. 8, pages 1,685-2,687 (1991); J. Am. Chem. Soc., Volume 123, page 4,304 (2001); Inorganic Chemistry Volume 40, No. 7, pages 1,704-1,711; Inorganic Chemistry Volume 41, No. 12, pages 3,055-3,066 (2002); New Journal of Chemistry., Volume 26, page 1,171 (2002); Angewandte Chemie International Edition, Volume 38, pages 1,698-1,712 (1999); Bulletin of the Chemical Society of Japan, Volume 71, pages 467-473 (1998); J. Am. Chem. Soc., Volume 125, No. 18, 5274-5275 (2003); and J. Am. Chem. Soc., Volume 125, No. 35, 10580-10535 (2003), as well as references cited therein.

Example 2

Preparation of Organic EL Element 1-1

Present Invention

A substrate (NA-45, produced by NH Techno Glass Corp.), which was prepared in such a manner that ITO (indium tin oxide) was applied onto a 100 mm×100 mm×1.1 mm glass substrate to form a 100 nm thick film as an anode, was subjected to patterning. Thereafter, a transparent supporting substrate provided with the above ITO transparent electrode was subjected to ultrasonic cleaning employing isopropyl alcohol, followed by drying via desiccated nitrogen gas and cleaning via UV ozone for 5 minutes.

A solution, prepared by diluting poly(3,4-ethylenedioxythiophene)-polystyrene sulfonate (PEDOT/PSS, BAYTRON P Al 4083, produced by Bayer Co.) with pure water to reach 70% by weight, was applied onto the above supporting transparent substrate at 3,000 rpm for 30 seconds via a spin coating method so that a film was formed, followed by drying at 200° C. for one hour, whereby a 30 nm thick first positive hole transporting layer was prepared.

A solution, which was prepared by dissolving 30 mg of m-CP and 1.5 mg of BD-6 in 3 ml of toluene, was applied onto the above first positive hole transporting layer at 1,000 rpm for 30 seconds via a spin coating method, followed by vacuum drying at 60° C. for one hour, whereby a 80 nm thick light emitting layer was prepared.

The resulting product was attached to a vacuum deposition apparatus. Subsequently, the pressure of the vacuum tank was reduced to $4\times10^{-4}$ Pa, and 10 nm calcium and 110 nm aluminum were deposited as a cathode buffer layer to form a cathode, whereby Organic EL Element 1-1 was prepared.

<<Preparation of Organic EL Elements 1-2-1-4 and 1-6>>: Present Invention

Each of Organic EL elements 1-2-1-4 and 1-6 was prepared in the same manner as Organic EL element 1-1, except that BD-6, which was employed to prepare the light emitting layer, was replaced with BD-28, BD-42, ED-547, or BD-56.

<<Preparation of Organic EL Element 1-5>>: Comparative Example

Organic EL Element 1-5 was prepared in the same manner as Organic EL Element 1-1, except that 3 ml of the BD-6 toluene solution was replaced with 3 ml of a ED-546 tetrahydrofuran (THF) solution.

<<Evaluation of Organic EL Elements 1-1-1-6>>

Prepared Organic EL Elements 1-1-1-6 were evaluated as follows. The non-light emitting surface of each organic EL element was covered with a glass enclosure. A 300 μm thick glass substrate was employed as a sealing substrate. It was overlapped on the above cathode and was brought into tight contact with the above transparent supporting substrate, employing an epoxy based light curable type adhesive (LACKSTRACK LC029B, produced by Toagosei Co., Ltd.), as a peripheral sealing material. Subsequently, the glass substrate surface was exposed to UV radiation to result in curing and sealing, whereby illuminating devices shown in FIGS. 3 and 4 were prepared, followed by evaluation.

Figure 3:
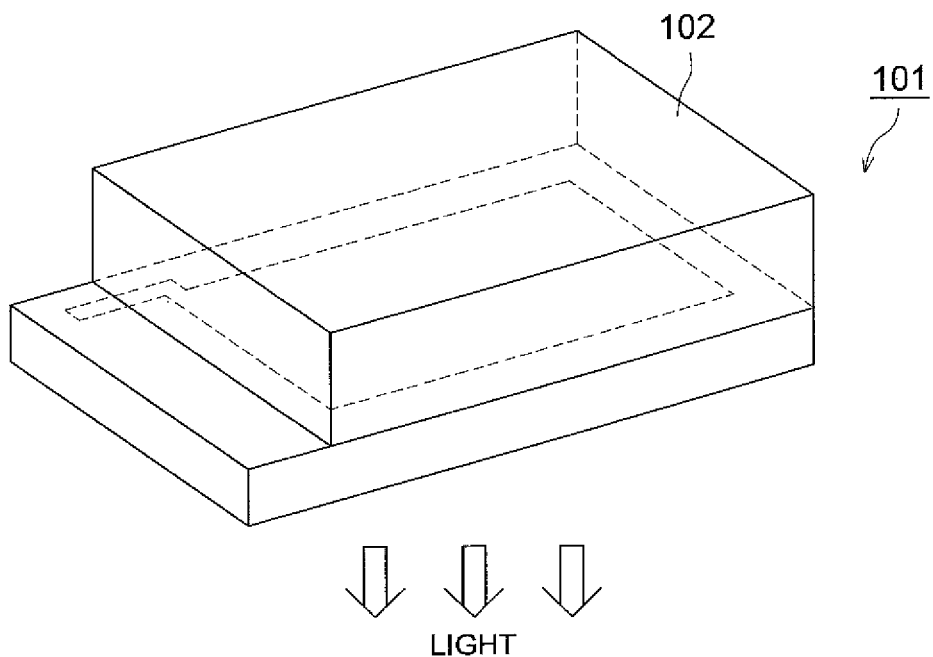
FIG. 3 is a schematic view of an illuminating device.

FIG. 3 is a schematic view of an illuminating device, and organic EL element 101 is covered with glass cover 102. Sealing via the glass cover was carried out in a glove box (in an ambience of high purity nitrogen gas at a purity of at least 99.999%) so that organic EL element 101 was not contact with the ambient atmosphere. FIG. 4 is a cross-sectional view of an illuminating device. In FIG. 4, 105 represents a cathode, 106 represents an organic EL layer, and 107 represents a glass substrate fitted with a transparent electrode. The interior of glass cover 102 was filled with nitrogen gas 108 and desiccating agent 109 is provided.

<<External Extraction Quantum Yield>>

A constant electric current of 2.5 mA/cm² was applied to each of the prepared organic EL elements at 23° C. under an ambience of desiccated nitrogen gas, and the external extraction quantum yield (in %) was determined. Determination was carried out by employing a spectral radiance meter CS-1000 (produced by Konica Minolta Inc.).

<<Light Emitting Lifetime>>

During driving via application of a constant electric current of 2.5 MA/cm² at 23° C. under an ambience of desiccated nitrogen gas, determined was the time which had passed until luminance decreased to one-half from that immediately after light emission (initial luminescence). The resulting value was designated as the half-decay time ($\tau^{1/2}$) which was employed as an index of lifetimes Determination was also carried out by employing a spectral radiance meter CS-1000 (produced by Konica Minolta Inc.).

Determination results of the external extraction quantum yield and the light emitting lifetime of Organic EL Elements 1-1-1-6 were subjected to relative comparison, with the value of Organic EL element 1-5 set at 100.

Table 1 shows the results.

TABLE 1

| Organic EL Element | External Extraction Quantum Yield (Relative Value) | Light Emitting Lifetime (Relative Value) | Remarks |
| --- | --- | --- | --- |
| 1-1 | 118 | 500 | Present Invention |
| 1-2 | 121 | 480 | Present Invention |
| 1-3 | 115 | 210 | Present Invention |
| 1-4 | 106 | 101 | Present Invention |
| 1-5 | 100 | 100 | Comparative Example |
| 1-6 | 106 | 1000 | Present Invention |

As is clearly seen from Table 1, compounds (also referred to as metal complexes), which are employed as a light emitting dopant, are suitable to prepare organic EL elements via a coating method due to enhancement of the solubility and film producing properties. As a result, it is clear that in Organic EL Elements 1-1-1-4, light emitting efficiency is enhanced and specifically, light emitting lifetime is significantly enhanced.

Further, when an aromatic hydrocarbon group having a substituent or an aromatic heterocyclyl group having a substituent is provided to Organic EL Element 1-4, in which an alkyl group is only employed as a solubility controlling group or a film formation controlling group (no data are shown in Table 3), the light emitting lifetime is markedly enhanced, though it is assumed that rigidity of the core structure which becomes a light emitting center is enhanced.

Example 3

Preparation of Organic EL Element 2-1

A substrate (NA-45, produced by NH Techno Glass Corp.) prepared in such a manner that ITO (indium tin oxide) was applied onto a 100 mm×100 mm×1.1 mm glass substrate to form a 100 nm thick film as an anode, was subjected to patterning. Thereafter, a transparent supporting substrate provided with the above ITO transparent electrode was subjected to ultrasonic cleaning employing isopropyl alcohol, followed by drying via desiccated nitrogen gas and cleaned with UV ozone for 5 minutes.

A solution, which was prepared by diluting poly(3,4-ethylenedioxythiophene)-polystyrene sulfonate (PEDOT/PSS, BAYTRON P Al 4083, produced by Bayer Co.) with pure water to reach 70% by weight, was applied onto the above supporting transparent substrate at 3,000 rpm for 30 seconds via a spin coating method so that a film was formed, followed by drying at 200° C. for one hour, whereby a 30 nm thick first positive hole transporting layer was prepared.

A solution, which was prepared by dissolving 30 mg of BD-180 in 3 ml of toluene, was applied onto the above first positive hole transporting layer at 3,000 rpm for 30 seconds via a spin coating method, followed by vacuum drying at 60° C. for one hour, whereby a 30 nm thick light emitting layer was prepared.

The resulting product was attached to a vacuum deposition apparatus. Subsequently, the pressure of the vacuum tank was reduced to $4\times10^{-4}$ Pa, and 50 nm bis(2-methyl-8-quinolato)-p-phenylphenolato-aluminum complex (BAlq) calcium was deposited to form an electron transporting layer. Subsequently, 1 nm lithium fluoride as a cathode buffer layer, and 110 nm aluminum as a cathode were deposited to form a cathode, whereby Organic EL Element 2-1 was prepared.

<<Preparation of Organic EL Element 2-2>>

Organic EL Element 2-2 was prepared in the same manner as Organic EL element 2-1, except that the solution prepared by dissolving 30 mg of ED-180 in 3 ml of tetrahydrofuran (THF), which was employed to prepare the light emitting layer, was replaced with a solution prepared by dissolving 3 mg of BD-546 in 3 ml of tetrahydrofuran (THF), and film was prepared via a spin coating method at conditions of 500 rpm and 30 seconds, followed by vacuum drying at 60° C. for one hour, whereby a 30 nm thick light emitting layer was prepared.

<<Evaluation of Organic EL Elements 2-1 and 2-2>>

Each of prepared Organic EL Elements 2-1 and 2-2 was evaluated in the same manner as described in Example 2. Measurement results of the external extraction quantum yield and the light emitting lifetime were subjected to relative evaluation when Organic EL element 2-2 was set at 100. Table 2 below shows the results.

TABLE 2

| Organic EL Element | External Extraction Quantum Yield (Relative Value) | Light Emitting Lifetime (Relative Value) | Remarks |
| --- | --- | --- | --- |
| 2-1 | 80 | 1200 | Present Invention |
| 2-2 | 100 | 100 | Comparative Example |

As can be seen from Table 2, Organic EL Element 2-1, which incorporates the novel compound of the present invention, exhibits a high external extraction quantum yield and the targeted long lifetime, compared to the comparative example. Specifically, in comparison with Organic EL Element 2-2 which is Comparative Example, when the light emitting layer is composed of only light emitting dopants as Organic EL Element 2-2 (Comparative Example), light emitting efficiency decreases due to concentration quenching since the concentration of light emitting dopants in the light emitting layer markedly increases.

However, it is found that in Organic EL Element 2-1 which employs, as a dopant, the novel compound (also referred to as the metal complex) of the present invention, which incorporates a solubility controlling group or a film formation controlling group as a partial structure which constitute the above compound, it is possible to realize an element of high efficiency, whereby it is possible to play a big role to simplify element constituting materials.

Example 4

Preparation of Full-Color Display Device (Blue Light Emitting Organic EL Element)

Organic EL Element 1-1, which was prepared in Example 2, was employed as a blue light emitting organic EL element.

(Green Light Emitting Organic EL Element)

Green Light Emitting Organic EL Element 1-1G (green) was prepared in the same manner as Organic EL Element 1-1 in Example 2, except that BED-G was replaced with PD-1.

(Red Light Emitting Organic EL Element)

Red Light Emitting Organic EL Element 1-1R (red) was prepared in the same manner as Organic EL Element 1-1 in Example 3, except that ED-6 was replaced with PD-6.

Figure 2:
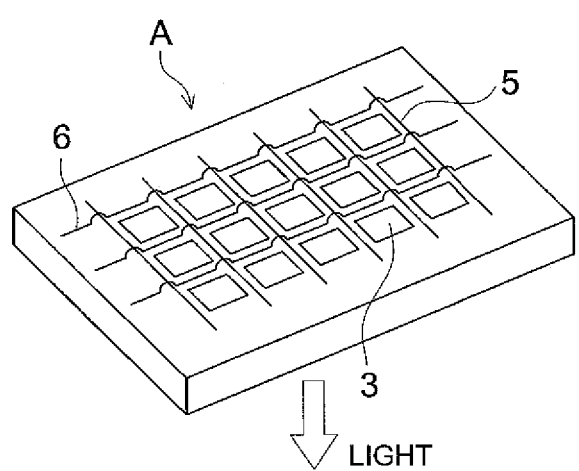
FIG. 2 is a schematic view of a display section.

Above red, green, and blue light emitting EL elements were arranged in parallel on the same substrate, and an active matrix system full-color display device, shown in FIG. 1, was prepared. In FIG. 2, only shown is the schematic view of display section A of the above prepared display device. Namely, on the same substrate, arranged are a wiring section incorporating a plurality of scanning lines 5 and data lines 6, and a plurality of pixels 3 (pixels of their emitting light in the red region, pixels of their emitting light in the green region, and pixels of their emitting light in the blue region). Each of scanning lines 5 and a plurality of data lines 6 is composed of electrically conductive materials. Scanning lines 5 and data lines 6 cross perpendicularly to each other and connect to pixel 3 at the crossing (no detail of which is shown). Each of a plurality of above pixels 3 is driven via an active matrix system, in which the organic EL element corresponding to each of the emitted light colors, as well as a switching transistor and a driving transistor which are active elements, are arranged. When scanning signals are applied from scanning line 5, image data signals are received from data line 6, and in response to the above received image data, light is emitted. As described above, by appropriately arranging each of the red, green, and blue pixels in parallel, a full-color display device was prepared.

By driving the above full-color display device, it was confirmed that it was possible to realize a full-color moving image display of high light emitting efficiency and long light emitting lifetime.

Example 5

Preparation of White Light Illuminating-Device

White Light Emitting Organic EL Element 1-1W (white) was prepared in the same manner as Organic EL Element 1-1 in Example 3, except that BD-5 was replaced with BD-6, PD-1, and PD-6.

Resulting Organic EL Element 1-1W was employed as follows. The non-light emitting surface was covered with a glass enclosure in the same manner as Example 1, to prepare an illuminating device. It was possible to employ the resulting illuminating device as a thin illuminating device of high light emitting efficiency and emitted white light over a long light emitting lifetime.

What is claimed is:

1. A compound characterized by having a partial structure represented by Formula (2),

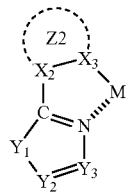

Formula (2)

wherein $X_2$ and $X_3$ each represents a carbon atom;
$Y_1$ represents —$N(R_1)$—;
$Y_2$ and $Y_3$ each represents a carbon atom;
Z2 represents a group of atoms which are necessary to form a 6-membered aromatic hydrocarbon ring, or a group of atoms which are necessary to form a 5- to 6-membered aromatic heterocyclic ring;
M represents Ir or Pt;
$R_1$ represents a hydrogen atom, an alkyl group, an alkenyl group, an alkynyl group, or a cycloalkyl group; and
the partial structure has at least two of a solubility controlling group or a film formation controlling group, and the solubility controlling group or the film formation controlling group represents an aromatic hydrocarbon group having a substituent, an aromatic heterocyclyl group having a substituent, or an alkyl group having at least 6 carbon atoms.

2. A compound characterized by having a partial structure represented by Formula (2),

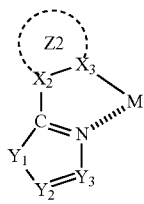

wherein $X_2$ and $X_3$ each represents a carbon atom;
$Y_1$ represents —$N(R_1)$—;
$Y_2$ and $Y_3$ each represents a carbon atom;
Z2 represents a group of atoms which are necessary to form a 6-membered aromatic hydrocarbon ring, or a group of atoms which are necessary to form a 5- to 6-membered aromatic heterocyclic ring;
M represents Ir or Pt;
$R_1$ represents a hydrogen atom, an alkyl group, an alkenyl group, an alkynyl group, a cycloalkyl group, an aromatic hydrocarbon ring, an aromatic heterocyclyl group, or a heterocyclyl group;
the partial structure has at least two of a solubility controlling group or a film formation controlling group, one of which is substituted on the carbon atom represented by $Y_2$; and
the solubility controlling group or the film formation controlling group represents an aromatic hydrocarbon group having a substituent, an aromatic heterocyclyl group having a substituent, or an alkyl group having at least 6 carbon atoms.

3. An organic electroluminescent element comprising a support substrate having thereon at least an anode, a cathode, and one or more organic layers between the anode and the cathode, wherein
the one or more organic layers include at least one light emitting layer and
at least one of the one or more organic layers contains the compound according to claim 1.

4. An illuminating device comprising the organic electroluminescent element according to claim 3.

5. A display device comprising the organic electroluminescent element according to claim 3.

6. An organic electroluminescent element comprising a support substrate having thereon at least an anode, a cathode, and one or more organic layers between the anode and the cathode, wherein
the one or more organic layers include at least one light emitting layer and
at least one of the one or more organic layers contains the compound according to claim 2.

7. An illuminating device comprising the organic electroluminescent element according to claim 6.

8. A display device comprising the organic electroluminescent element according to claim 6.

9. An organic electroluminescent element comprising a support substrate having thereon at least an anode, a cathode, and one or more organic layers between the anode and the cathode, wherein
the one or more organic layers include one or more light emitting layers, and
at least one of the one or more light emitting layers contains the compound according to claim 1.

10. An organic electroluminescent element comprising a support substrate having thereon at least an anode, a cathode, and one or more organic layers between the anode and the cathode, wherein
the one or more organic layers include one or more light emitting layers, and
at least one of the one or more light emitting layers contains the compound according to claim 2.

* * * * *